(12) United States Patent
Sternby et al.

(10) Patent No.: US 11,433,167 B2
(45) Date of Patent: Sep. 6, 2022

(54) CONNECTION TEST FOR BLOOD TREATMENT MACHINES

(71) Applicant: GAMBRO LUNDIA AB, Lund (SE)

(72) Inventors: Jan Sternby, Lund (SE); Björn Ericson, Lund (SE)

(73) Assignee: Gambro Lundia AB, Lund (SE)

(*) Notice: Subject to any disclaimer, the term of this patent is extended or adjusted under 35 U.S.C. 154(b) by 946 days.

(21) Appl. No.: 16/307,093

(22) PCT Filed: Jun. 27, 2017

(86) PCT No.: PCT/EP2017/065770
§ 371 (c)(1),
(2) Date: Dec. 4, 2018

(87) PCT Pub. No.: WO2018/001996
PCT Pub. Date: Jan. 4, 2018

(65) Prior Publication Data
US 2020/0306437 A1    Oct. 1, 2020

(30) Foreign Application Priority Data
Jun. 30, 2016 (SE) .................................. 1650950-7

(51) Int. Cl.
*A61M 1/16* (2006.01)
*A61M 1/36* (2006.01)

(52) U.S. Cl.
CPC ........ *A61M 1/1601* (2014.02); *A61M 1/1647* (2014.02); *A61M 1/3656* (2014.02);
(Continued)

(58) Field of Classification Search
CPC ........ A61M 1/14; A61M 1/16; A61M 1/1601; A61M 1/1603; A61M 1/1605;
(Continued)

(56) References Cited

U.S. PATENT DOCUMENTS 4,468,219 A   8/1984   George et al.
5,024,756 A   6/1991   Sternby
(Continued)

FOREIGN PATENT DOCUMENTS

CA   2785758   7/2011
EP   0658352   6/1995
(Continued)

OTHER PUBLICATIONS

International Search Report for International Application No. PCT/EP2017/065770, dated Aug. 31, 2017; (3 pages).

*Primary Examiner* — Amber R Stiles
*Assistant Examiner* — Avery Smale
(74) *Attorney, Agent, or Firm* — K&L Gates LLP

(57) ABSTRACT

A control device for a blood treatment machine performs a connection test (50) by causing the blood treatment machine to switch (51, 53) between a first and a second operating state by reversing a blood pump so as to change a flow direction of blood through both a dialyzer and access devices connected to a patient. Based on an output signal of at least one sensor in the blood treatment machine (52, 54), the control device computes (55) an efficiency change parameter that represents a change in in-vivo clearance of the blood treatment machine during the switch of the blood treatment machine between the first and second operating states. The control device evaluates (56) the efficiency change parameter to jointly detect connection errors at the dialyzer, resulting in co-current flow of treatment fluid and blood through the dialyzer, and at the access devices, resulting in access recirculation of blood.

24 Claims, 8 Drawing Sheets

(52) U.S. Cl.
CPC . *A61M 2205/18* (2013.01); *A61M 2205/3334* (2013.01); *A61M 2205/3368* (2013.01)

(58) Field of Classification Search
CPC .. A61M 1/1647; A61M 1/305; A61M 1/3621; A61M 1/3656; A61M 2205/18; A61M 2205/3334; A61M 2205/3368; A61M 2205/70
See application file for complete search history.

(56) References Cited

U.S. PATENT DOCUMENTS

| | | | |
|---|---|---|---|
| 5,100,554 A | 3/1992 | Polaschegg | |
| 6,702,774 B1 | 3/2004 | Polaschegg et al. | |
| 7,896,831 B2 | 3/2011 | Sternby et al. | |
| 2006/0116624 A1* | 6/2006 | Sternby | A61M 1/1613 604/5.01 |
| 2008/0015487 A1* | 1/2008 | Szamosfalvi | A61M 1/3675 210/323.1 |
| 2009/0171261 A1 | 7/2009 | Sternby et al. | |
| 2011/0196279 A1 | 8/2011 | Maierhofer et al. | |
| 2013/0026098 A1* | 1/2013 | Haecker | A61M 1/16 210/97 |
| 2013/0193039 A1* | 8/2013 | Kopperschmidt | A61M 1/16 73/170.01 |
| 2013/0338560 A1* | 12/2013 | Bene | A61M 1/3656 604/6.09 |
| 2014/0199193 A1* | 7/2014 | Wilt | A61M 1/3609 417/474 |
| 2014/0291565 A1 | 10/2014 | Maierhofer et al. | |

FOREIGN PATENT DOCUMENTS

| | | |
|---|---|---|
| EP | 1938847 | 7/2008 |
| WO | WO 2012016671 | 9/2012 |
| WO | WO 2016016039 | 2/2016 |

* cited by examiner

CONNECTION TEST FOR BLOOD TREATMENT MACHINES

PRIORITY CLAIM

The present application is a National Phase of International Application No. PCT/EP2017/065770, filed Jun. 27, 2017, which claims priority to Swedish Patent Application No. 1650950-7, filed Jun. 30, 2016, the entire contents of each of which are incorporated herein by reference and relied upon.

TECHNICAL FIELD

The present invention relates to treatment of chronic renal failure, and in particular a technique of checking that a blood treatment machine is set up with correct flow directions before treatment.

BACKGROUND ART

In treating chronic renal failure, various methods of purification and treatment of blood with machinery are used to replace the function of a healthy kidney. Such methods typically aim at withdrawing fluid and removing substances from the blood, and may also involve adding fluid and substances to the blood. Such purification and treatment may be performed by pumping a treatment fluid and blood through dedicated chambers of a blood filtration unit, commonly denoted a dialyzer. The treatment fluid chamber and the blood chamber of the dialyzer are separated by a semi-permeable membrane. While blood and treatment fluid flows on opposite sides of the membrane, fluid and substances are transported between the treatment fluid and the blood over the semi-permeable membrane. Diffusive mass transport through the membrane is predominant in hemodialysis (HD), whereas hemofiltration (HF) uses mainly convective mass transport through the membrane. Hemodiafiltration (HDF) is a combination of the two methods.

Machines for treatment of chronic renal failure, denoted "dialysis machines" in the following, comprise a first flow circuit which is connected to dedicated inlet and outlet connectors on the dialyzer and is configured to supply treatment fluid and pump the treatment fluid through the treatment fluid chamber, and a second flow circuit which is connected to the subject by an access device for blood withdrawal (e.g. an arterial needle or catheter adapter) and an access device for blood reintroduction (e.g. a venous needle or catheter adapter), which are connected to a dedicated blood vessel access (e.g. fistula, graft or catheter) on the subject. The second flow circuit is further connected to dedicated inlet and outlet connectors on the dialyzer and comprises a blood pump which is operable to draw blood from the subject via the access device for blood withdrawal, pump the blood through the blood chamber of the dialyzer and return the thus-treated blood to the subject via the access device for blood return. The second flow circuit is commonly referred to as an extracorporeal blood flow circuit.

Maximum efficiency of the exchange process over the semi-permeable membrane in the dialyzer is achieved by having the blood and the treatment fluid flow in opposite directions along the membrane ("counter-current configuration"). If the blood and the treatment fluid flow in the same direction ("co-current configuration"), a lower dialysis efficiency is achieved. Thus, in practice, the dialyzer is connected to the first and second flow circuits in the counter-current configuration.

It should be understood that the dialyzer is a disposable, which is regularly replaced by the operator of the dialysis machine. Further, the second flow circuit is at least partly formed by a second disposable which also needs to be regularly replaced by the operator of the dialysis machine. Typically, the second disposable comprises a set of blood lines, or a dedicated cassette. The second disposable may, but typically does not, include the blood pump. Instead, in current dialysis machines, the blood pump (e.g. a peristaltic pump) is integrated in a machine chassis that also hosts the first flow circuit, and the second disposable is attached onto the machine chassis in operative engagement with the blood pump, such that the blood pump is operable to displace blood through the second disposable.

As understood from the foregoing, it may be important to ensure after each replacement of one or more of the above-mentioned disposables that the dialyzer has been correctly connected to the first and second flow circuits, and specifically to avoid a co-current configuration of the dialyzer.

This problem is addressed by WO2012/016671, which proposes a technique for detecting the flow directions through a dialyzer. The technique is based on the following sequence of steps: producing a first bolus change in temperature or concentration in the treatment fluid provided to the dialyzer, measuring a corresponding first change in temperature or concentration downstream of the dialyzer, switching the direction of fluid flow through the dialyzer, producing a second bolus change in temperature or concentration in the treatment fluid provided to the dialyzer, and measuring a corresponding second change in temperature or concentration downstream of the dialyzer. The actual detection of the flow directions through the dialyzer is executed by computing integrals of the first and second bolus changes and the corresponding first and second changes, computing dialysance values before and after the switching based on the integrals, and analyzing the ratio of the dialysance values after and before the switching. If the ratio is smaller than 1, it is concluded that the dialyzer was operated in a counter-current configuration before the switching. Otherwise, it is concluded that the dialyzer was operated in a co-current configuration before the switching. WO2012/016671 proposes to achieve the switching of flow direction by reversing the flow direction of the treatment fluid through the dialyzer, but also mentions that it is in principle possible to instead reverse the flow direction of the blood. It is also briefly stated that the flow reversal may be achieved by switching a valve arrangement to locally reverse the flow through the dialyzer or by reversing a pump to reverse the flow throughout the fluid circuit.

There is a continued need to improve the safety of dialysis machines and ensure that the patient gets the prescribed dialysis treatment. For example, the treatment efficiency may be significantly reduced if the operator inadvertently connects the access devices to the vascular access in a reversed placement with respect to the blood flow through the vascular access, i.e. such that the extracorporeal blood flow circuit draws blood from an downstream position of the vascular access and returns treated blood to an upstream position of the vascular access. The reversed placement will caused so-called recirculation, in which the extracorporeal blood flow circuit will take up some of the already treated blood entering the vascular access, leading to poor treatment results.

SUMMARY

It is an objective of the invention to at least partly overcome one or more of limitations of the prior art.

Another objective is to provide a technique for detecting connection errors of a blood treatment machine, both at the dialyzer and at the vascular access.

Yet another objective is to provide such a technique which is simple to implement.

One or more of these objectives, as well as further objectives that may appear from the description below, are at least partly achieved by a control device, a blood treatment machine, a method and a computer-readable medium, embodiments thereof being defined by the dependent claims.

A first aspect of the invention is a control device for a blood treatment machine. The blood treatment machine comprises an extracorporeal blood flow circuit with first and second access devices for connection to upstream and downstream portions, respectively, of a vascular access of a patient and having a blood pump operable to generate a flow of blood in the extracorporeal blood flow circuit from one of the first and second access devices through a blood compartment of a dialyzer and to another of the first and second access devices. The blood treatment machine further comprises a treatment fluid flow circuit configured to generate a flow of treatment fluid through a treatment fluid compartment of the dialyzer, the treatment fluid compartment being separated from the blood compartment by a semi-permeable membrane. The control device is configured to, during a connection test: cause the blood treatment machine to switch between a first operating state in which the blood pump is operated in a default direction to pump the blood from the first access device through the blood compartment of the dialyzer to the second access device, and a second operating state in which the blood pump is operated in a reverse direction to pump the fluid from the second access device through the blood compartment of the dialyzer to the first access device; acquire an output signal of at least one sensor in the blood treatment machine; compute, based on the output signal, an efficiency change parameter that represents a change in in-vivo clearance of the blood treatment machine during the switch of the blood treatment machine between the first and second operating states; and evaluate the efficiency change parameter to determine if the first or second operating state involves a dual fault condition comprising both a co-current dialyzer configuration, in which the flow of blood through the blood compartment and the flow of treatment fluid through the treatment fluid compartment are in a common direction along the semi-permeable membrane, and a reversed access device configuration, in which the first and second access devices are connected to the downstream and upstream portions, respectively, of the vascular access.

The first aspect is based on the insight that a reversed placement of the access devices may be detected by monitoring the change in in-vivo clearance of the blood treatment machine, via an efficiency change parameter, during a reversal of the flow direction of blood through the access devices. The first aspect is also based on the insight that it is actually possible to jointly detect connection errors at the dialyzer and connection errors at the access devices by merely reversing the pumping direction of the blood pump, since this will change the flow direction of blood in both the dialyzer and through the access devices. The reversal of the blood pump will either switch the blood treatment machine between the dual fault condition and a correct condition, or between a respective single fault condition. According to the first aspect, the efficiency change parameter is evaluated to detect if one of the first and second operating states is in the dual fault condition. If the evaluation allocates the dual fault condition to the second operating state, the first operating state is in the correct condition, and vice versa. If the evaluation allocates the dual fault condition to neither of the first and second operating states, the first operating state is in one of the single fault conditions. Thus, the first aspect allows the control unit to detect connection errors at both the dialyzer and the access devices, and also to verify a correct connection at both the dialyzer and the access devices.

The first aspect is simple to implement since it merely requires the blood pump to be switchable between a forward and a reverse direction. There is no need to install expensive and potentially complex valve arrangements for flow reversal in the extracorporeal blood flow circuit or the treatment fluid flow circuit. In fact, the control unit of the first aspect may be installed to implement the connection test in any blood treatment machine with reversible blood pump.

It should be the noted that the control device may be configured to cause the blood treatment machine to switch between the first operating state and the second operating state by prompting an operator to manually set the machine in the respective state, e.g. by manipulating the blood pump. Alternatively, the control device may be configured to switch the blood treatment machine between the first and second operating states by generating a dedicated control signal for the blood pump.

In one embodiment, the control device is further configured to generate a first warning signal indicating that the blood treatment machine has failed the connection test, if the first operating state is determined to involve the dual fault condition. In one embodiment, the control device is operatively associated with an interface device configured to output instructions for an operator of the blood treatment machine, wherein the control device is configured to, if the first operating state is determined to involve the dual fault condition, operate the interface device to instruct the operator to change a connection of the treatment fluid flow circuit or the extracorporeal blood flow circuit to the dialyzer and to change a connection of the first and second access devices to the vascular access.

In one embodiment, the control device is further configured to generate a confirmation signal indicating that the blood treatment machine has passed the connection test, if the second operating state is determined to involve the dual fault condition.

In one embodiment, the control device is further configured to selectively enable the blood treatment machine to perform a blood treatment session, if the second operating state is determined to involve the dual fault condition.

In one embodiment, the control device is further configured to compare the efficiency change parameter to a first range indicating the dual fault condition in the first operating state, a second range indicating the dual fault condition in the second operating state, a third range indicating the co-current dialyzer configuration and not the reversed access device configuration in the first operating state, and a fourth range indicating the reversed access device configuration and not the co-current dialyzer configuration in the first operating state.

In one embodiment, the control device is further configured to evaluate the efficiency change parameter to determine if the first and second operating states involve a respective single fault condition comprising either the co-current dialyzer configuration or the reversed access device configuration. The control device may be further configured to generate a second warning signal for an operator of the blood treatment machine, if the first and second operating states are determined to involve the single fault condition. Alternatively or additionally, the control device may be configured to, if the first and second operating states are determined to involve the single fault condition, instruct the operator to check connections of the treatment fluid flow circuit and the extracorporeal blood flow circuit to the dialyzer and a connection of the first and second access devices to the vascular access. Alternatively or additionally, the control device may be further configured to compare the efficiency change parameter to a first range indicating the dual fault condition in the first operating state, a second range indicating the dual fault condition in the second operating state, and a third range indicating the single fault condition in each of the first and second operating states. Further, a fourth range may be defined between the first and third ranges, and a fifth range may be defined between the second and third ranges, and the control device may be further configured to, if the efficiency change parameter falls within the fourth or fifth ranges, instruct the operator to indicate a mass transfer area coefficient of the dialyzer.

In one embodiment, the control device is further configured to obtain status values defining one or more of an estimated cardiac output of the patient, an estimated blood flow rate in the vascular access of the patient, a mass transfer area coefficient of the dialyzer, the flow rate of blood through the blood compartment of the dialyzer during the first and second operating states, and the flow rate of treatment fluid through the treatment fluid compartment of the dialyzer during the first and second operating states, and determine at least one of the above-mentioned ranges as a function of the status values.

In one embodiment, the control device is further configured to obtain dedicated connection test settings for the blood pump and the treatment fluid flow circuit and apply the dedicated connection test settings for controlling the blood pump and the treatment fluid flow circuit during the first and second operation states. In one implementation, the control device is configured to apply the dedicated connection test settings to cause the blood pump, by the control signal, to generate a fixed and predefined flow rate of blood through the dialyzer during the first and second operating states, and to cause the treatment fluid flow circuit, by a further control signal, to generate a fixed and predefined flow rate of treatment fluid through the dialyzer during the first and second operating states. Alternatively or additionally, the control device may be further configured to cause the treatment fluid flow circuit, by the further control signal, to generate a fixed fluid property of the treatment fluid, as measured by the at least one sensor, during the first and second operating states. In one example, the predefined flow rate of blood is in the approximate range of 200-300 ml/min and/or the predefined flow rate of treatment fluid is in the approximate range of 200-400 ml/min.

In one embodiment, the control device is configured to compute the efficiency change parameter to represent a ratio of the in-vivo clearance of the blood treatment machine in the first and second operating states.

In one embodiment, the output signal represents a physical and/or chemical property of the treatment fluid measured by the at least one sensor downstream, and possibly upstream, of the dialyzer in the treatment fluid flow circuit.

In one embodiment, the property is one of a temperature and a concentration of a substance that is present in the blood and is capable of exchanging across the semi-permeable membrane.

In one embodiment, the at least one sensor is one of a concentration sensor, a temperature sensor, a conductivity sensor, an optical absorbance sensor, a polarimetry sensor and a density sensor.

A second aspect of the invention is a blood treatment machine, comprising an extracorporeal blood flow circuit with first and second access devices for connection to upstream and downstream portions, respectively, of a vascular access of a patient and having a reversible blood pump operable to generate a flow of blood from one of the first and second access devices through a blood compartment of a dialyzer and to another of the first and second access devices, a treatment fluid flow circuit configured to generate a flow of treatment fluid through a treatment fluid compartment of the dialyzer, and the control device according to the first aspect.

A third aspect of the invention is a method of performing a connection test of a blood treatment machine comprising an extracorporeal blood flow circuit with first and second access devices for connection to upstream and downstream portions, respectively, of a vascular access of a patient and having a blood pump operable to generate a flow of blood in the extracorporeal blood flow circuit from one of the first and second access devices through a blood compartment of a dialyzer and to another of the first and second access devices, and a treatment fluid flow circuit configured to generate a flow of treatment fluid through a treatment fluid compartment of the dialyzer, the treatment fluid compartment being separated from the blood compartment by a semi-permeable membrane. The method comprising the steps of: switching the blood treatment machine between a first operating state in which the blood pump is operated in a default direction to pump the blood from the first access device through the blood compartment of the dialyzer to the second access device, and a second operating state in which the blood pump is operated in a reverse direction to pump the fluid from the second access device through the blood compartment of the dialyzer to the first access device; computing, based on an output signal of at least one sensor in the blood treatment machine, an efficiency change parameter that represents a change in in-vivo clearance of the blood treatment machine when switched between the first and second operating states; and evaluating the efficiency change parameter to determine if the first or second operating state involves a dual fault condition comprising both a co-current dialyzer configuration, in which the flow of blood through the blood compartment and the flow of treatment fluid through the treatment fluid compartment are in a common direction along the semi-permeable membrane, and a reversed access device configuration, in which the first and second access devices are connected to the downstream and upstream portions, respectively, of the vascular access.

In one embodiment, the method further comprises: generating, if the first operating state is determined to involve the dual fault condition, a first warning signal indicating that the blood treatment machine has failed the connection test.

In one embodiment, the method further comprises: operating, if the first operating state is determined to involve the dual fault condition, an interface device to instruct an operator of the blood treatment machine to change a connection of the treatment fluid flow circuit or the extracorporeal blood flow circuit to the dialyzer and to change a connection of the first and second access devices to the vascular access.

In one embodiment, the method further comprises: generating, if the second operating state is determined to involve the dual fault condition, a confirmation signal indicating that the blood treatment machine has passed the connection test.

In one embodiment, the method further comprises: selectively enabling the blood treatment machine to perform a blood treatment session, if the second operating state is determined to involve the dual fault condition.

In one embodiment, the step of evaluating the efficiency change parameter comprises: comparing the efficiency change parameter to a first range indicating the dual fault condition in the first operating state, a second range indicating the dual fault condition in the second operating state, a third range indicating the co-current dialyzer configuration and not the reversed access device configuration in the first operating state, and a fourth range indicating the reversed access device configuration and not the co-current dialyzer configuration in the first operating state.

In one embodiment, the step of evaluating the efficiency change parameter comprises: evaluating the efficiency change parameter to determine if the first and second operating states involve a respective single fault condition comprising either the co-current dialyzer configuration or the reversed access device configuration. The method may further comprise: generating, if the first and second operating states are determined to involve the single fault condition, a second warning signal for an operator of the blood treatment machine. Alternatively or additionally, the method may further comprise: instructing, if the first and second operating states are determined to involve the single fault condition, the operator to check connections of the treatment fluid flow circuit and the extracorporeal blood flow circuit to the dialyzer and a connection of the first and second access devices to the vascular access. Alternatively or additionally, the step of evaluating the efficiency change parameter may comprise: comparing the efficiency change parameter to a first range indicating the dual fault condition in the first operating state, a second range indicating the dual fault condition in the second operating state, and a third range indicating the single fault condition in each of the first and second operating states. Further, the method may further comprise: instructing, if the efficiency change parameter falls within a fourth range between the first and third ranges or within a fifth range between the second and third ranges, the operator to indicate a mass transfer area coefficient of the dialyzer.

In one embodiment, the method further comprises: obtaining status values defining one or more of an estimated cardiac output of the patient, an estimated blood flow rate in the vascular access of the patient, a mass transfer area coefficient of the dialyzer, the flow rate of blood through the blood compartment of the dialyzer during the first and second operating states, and the flow rate of treatment fluid through the treatment fluid compartment of the dialyzer during the first and second operating states, and determining at least one of the above-mentioned ranges as a function of the status values.

In one embodiment, the method further comprises: obtaining dedicated connection test settings for the blood pump and the treatment fluid flow circuit, and applying the dedicated connection test settings for controlling the blood pump and the treatment fluid flow circuit during the first and second operation states. In one implementation, the method further comprises: applying the dedicated connection test settings to cause the blood pump, by the control signal, to generate a fixed and predefined flow rate of blood through the dialyzer during the first and second operating states, and to cause the treatment fluid flow circuit, by a further control signal, to generate a fixed and predefined flow rate of treatment fluid through the dialyzer during the first and second operating states. Alternatively or additionally, the method may further comprise: causing the treatment fluid flow circuit, by the further control signal, to generate a fixed fluid property of the treatment fluid, as measured by the at least one sensor, during the first and second operating states. In one example, the predefined flow rate of blood is in the approximate range of 200-300 ml/min and/or the predefined flow rate of treatment fluid is in the approximate range of 200-400 ml/min.

In one embodiment, the efficiency change parameter is computed to represent a ratio of the in-vivo clearance of the blood treatment machine in the first and second operating states.

In one embodiment, the method further comprises: acquiring the output signal from the at least one sensor, the output signal representing a physical and/or chemical property of the treatment fluid measured by downstream, and possibly upstream, of the dialyzer in the treatment fluid flow circuit.

In one embodiment, the property is one of a temperature and a concentration of a substance that is present in the blood and is capable of exchanging across the semi-permeable membrane.

In one embodiment, the at least one sensor is one of a concentration sensor, a temperature sensor, a conductivity sensor, an optical absorbance sensor, a polarimetry sensor and a density sensor.

A fourth aspect of the invention is a computer-readable medium comprising computer instructions which, when executed by a processor, cause the processor to perform the method of the third aspect.

Any one of the above-identified embodiments of the first aspect may be adapted and implemented as an embodiment of the second to fourth aspects.

Still other objectives, features, aspects and advantages of the present invention will appear from the following detailed description, from the attached claims as well as from the drawings.

BRIEF DESCRIPTION OF THE DRAWINGS

Embodiments of the invention will now be described in more detail with reference to the accompanying schematic drawings.

DETAILED DESCRIPTION OF EXAMPLE EMBODIMENTS

Figure 1:
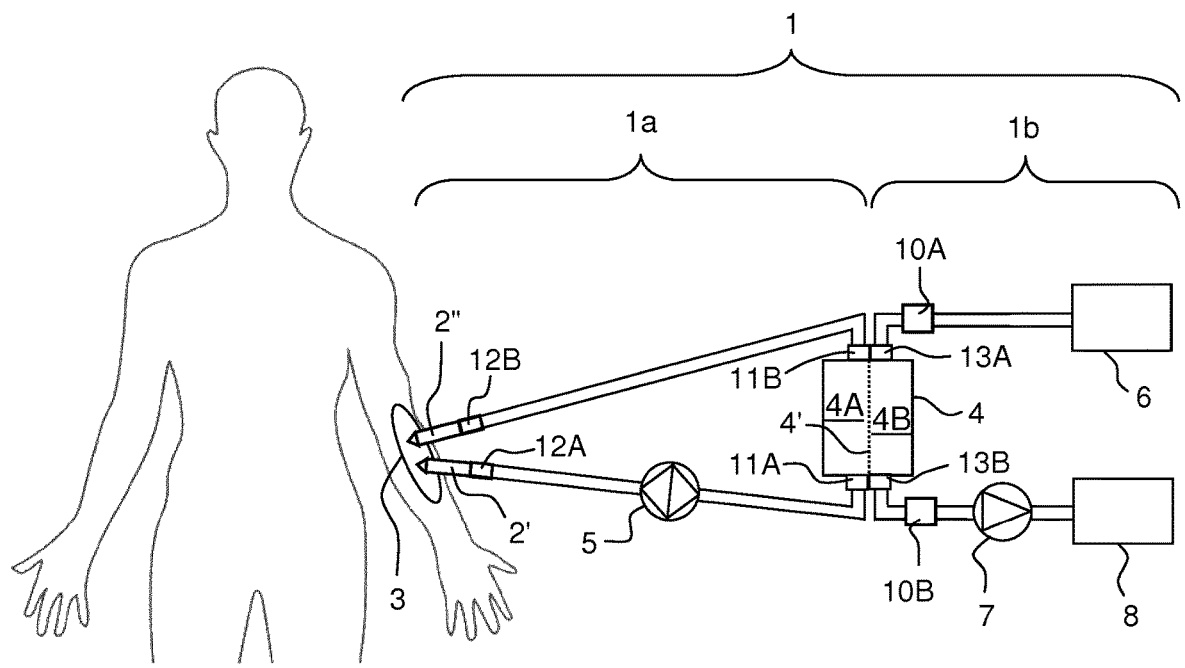
FIG. 1 is a schematic overview of a dialysis system connected to a patient.

Embodiments of the present invention will now be described more fully hereinafter with reference to the accompanying drawings, in which some, but not all, embodiments of the invention are shown. Indeed, the invention may be embodied in many different forms and should not be construed as limited to the embodiments set forth herein; rather, these embodiments are provided so that this disclosure may satisfy applicable legal requirements. Like numbers refer to like elements throughout.

Also, it will be understood that, where possible, any of the advantages, features, functions, devices, and/or operational aspects of any of the embodiments of the present invention described and/or contemplated herein may be included in any of the other embodiments of the present invention described and/or contemplated herein, and/or vice versa. In addition, where possible, any terms expressed in the singular form herein are meant to also include the plural form and/or vice versa, unless explicitly stated otherwise. As used herein, "at least one" shall mean "one or more" and these phrases are intended to be interchangeable. Accordingly, the terms "a" and/or "an" shall mean "at least one" or "one or more," even though the phrase "one or more" or "at least one" is also used herein. As used herein, except where the context requires otherwise owing to express language or necessary implication, the word "comprise" or variations such as "comprises" or "comprising" is used in an inclusive sense, that is, to specify the presence of the stated features but not to preclude the presence or addition of further features in various embodiments of the invention.

Before describing embodiments of the invention detail, a few further definitions will be given.

As used herein, "clearance" is given its ordinary meaning and is a measure of the purification efficiency of a dialyzer, typically given as ml/min Clearance may sometimes be defined to exclusively refer to removal, from the blood, of one or more substances that are absent in the fresh treatment fluid fed to the dialyzer, such as urea. The term "dialysance" may sometimes be used to designate an approximation of clearance so as to represent removal, from the blood, of one or more substances that are present also in the fresh treatment fluid, such as sodium or another electrolyte that passes the semi-permeable membrane of the dialyzer. With these definitions, the clearance and the dialysance will be equal for a given dialyzer in the absence of ultrafiltration. Within the present disclosure, no distinction is made between clearance and dialysance, and these terms are thus considered to be synonymous. Clearance may be measured directly on the dialyzer under well-controlled, non-patient specific, laboratory conditions. This type of clearance is commonly known as "in-vitro clearance" or "dialyzer clearance" and makes it possible to assess the relative efficacy of different dialyzers. Clearance may also be measured for a dialyzer under actual dialysis treatment conditions involving a patient. This type of clearance is commonly known as "in-vivo clearance" or "effective clearance" and is influenced by, e.g., the dialyzer, the effective blood flow rate, ultrafiltration, recirculation, and the flow rate of treatment fluid. Unless explicitly stated otherwise, the term clearance refers to the in-vivo clearance in the following description.

FIG. 1 illustrates a human subject or patient which is connected to an extracorporeal blood flow circuit $1a$ by way of access devices $2', 2''$ inserted into a dedicated vascular access 3 (also known as "blood vessel access") on the subject. The extracorporeal blood flow circuit $1a$ (denoted "EC circuit" in the following) is configured to draw blood from the vascular access 3 via access device $2'$ and pump the blood through a blood filter unit 4 and back to the vascular access 3 via access device $2''$. Thus, access device $2'$ is designated for blood withdrawal and access device $2''$ is designated for blood return. The vascular access 3 may be a fistula or a graft provided in the forearm of the patient, and the access devices $2', 2''$ may be needles or catheters, as is well-known in the art. The blood filter unit 4 may be any type of filtering device, such as a coil dialyzer, a parallel plate dialyzer, a hollow fiber dialyzer, etc. For simplicity, the blood filter unit 4 is denoted "dialyzer" in the following. The dialyzer 4 defines a blood chamber 4A and a treatment fluid chamber 4B separated by a semipermeable membrane $4'$.

The EC circuit $1a$ is part of an apparatus or machine 1 for blood treatment, such as a dialysis machine, at least when the machine 1 has been prepared for a treatment session. In the illustrated example, the EC circuit $1a$ comprises bloodlines connected to the access device $2', 2''$, a blood pump 5 and the blood chamber 4A of the dialyzer 4. As will be further described below, the blood pump 5 is operable in both a forward (default) direction and a reverse direction. The skilled person realizes that FIG. 1 is a simplified illustration and that the EC circuit $1a$ may comprise further components, such as a venous drip chamber, one or more pressure sensor, clamps, valves, etc.

The machine 1 further comprises a supply system $1b$ for treatment fluid (denoted "TF circuit" in the following). The TF circuit $1b$ is arranged to pump a treatment fluid through the treatment fluid side 4B of the dialyzer 4, while the blood pump 5 is operated to pump blood through the blood side 4A of the dialyzer 4, whereby solutes are transported over the membrane $4'$ due to a concentration gradient and/or ultrafiltrate is transported over the membrane $4'$ due to a pressure gradient. In the illustrated example, the TF circuit $1b$ comprises a source 6 of fresh treatment fluid (e.g. dialysis fluid), various fluid lines, the treatment fluid chamber 4B of the dialyzer 4, a treatment fluid pump 7, and is connected to a receptacle/drain 8 for receiving spent treatment fluid. The skilled person understands that the TF circuit $1b$ may include a plurality of other functional components such as further pumps, balancing chambers, valves, mixing chambers, heaters, etc. In the particular example of FIG. 1, the TF circuit also includes sensors 10A, 10B, which are configured to generate measurement signals that allow a control unit (not shown) to assess the dialysis efficiency, represented by the above-mentioned in-vivo clearance.

In practice, the machine 1 is typically formed as a combination of a permanent machine part and one or more disposables attached to the permanent machine part. The permanent machine part is enclosed in a machine chassis, often denoted "monitor", which exposes holders for mounting the disposable(s) in operative engagement with components such as connectors, pumps, sensors, clamps, etc. The disposables are exposed to the circulating blood in the EC circuit 1a and are typically discarded after each treatment session.

One such disposable is a bloodline set which includes the bloodlines of the EC circuit 1a, and connectors 11A, 11B on the bloodlines for coupling to dedicated inlet and outlet ports on the dialyzer 4, as indicated in FIG. 1. The access devices 2',2" may also be integrated with the bloodlines in the bloodline set. Alternatively, the access devices 2',2" may be provided as a separate disposable for connection to dedicated connectors 12A, 12B on the bloodlines, as indicated in the FIG. 1. The bloodline set may include further components, such as a venous drip chamber, valves, clamps, etc. For reasons of economy, components of the EC circuit 1a that are not exposed to the circulating blood are normally integrated in the machine chassis. For example, the blood pump 5 may be implemented as a peristaltic pump that engages with the exterior of a bloodline to push the blood though the bloodline, as is well known in the art. However, it is conceivable that the blood pump 5, if exposed to blood, is included in the disposable.

The dialyzer 4 may be provided as a separate disposable for installation on the machine chassis. When mounted on the machine chassis, the connectors 11A, 11B of the bloodline set are coupled to the dedicated inlet and outlet ports of the blood chamber 4A, and dedicated connectors 13A, 13B on the fluid lines of the TF circuit 1b are connected to dedicated inlet and outlet ports of the treatment fluid chamber 4B.

In an alternative, the dialyzer 4 is included in the bloodline set. In a further alternative, the bloodline set is replaced or supplemented by a cassette that defines internal fluid paths for blood. Such as cassette may also be integrated with the dialyzer 4.

Embodiments of the present invention addresses the risk that the operator of the machine 1 inadvertently makes an error when installing the dialyzer 4 in the machine 1, e.g. by confusing the connectors 11A, 11B or the connectors 13A, 13B. It is to be understood that the EC circuit 1a and the TF circuit 1b have a respective default pumping direction for blood and treatment fluid, respectively, so as to achieve a counter-current flow of blood and treatment fluid in the dialyzer 4. Thus, if the connectors 11A, 11B or 13A, 13B are confused, the machine 1 will inadvertently be operated in a co-current configuration. As explained in the Background section, this is undesirable since the co-current configuration results in lower dialysis efficiency than the counter-current configuration.

Figure 2A:
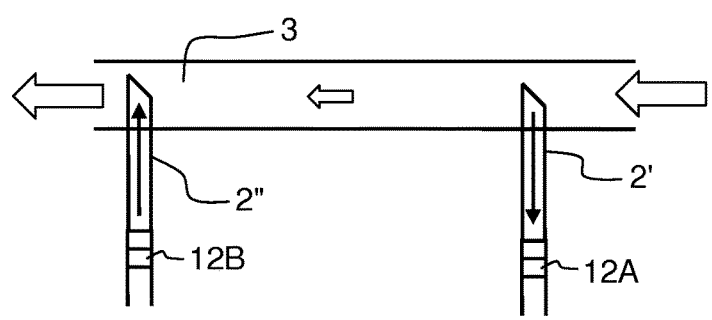
FIGS. 2A-2B are schematic side views of withdrawal and return devices in a normal and reversed configuration, respectively, at a vascular access.
Figure 2B:
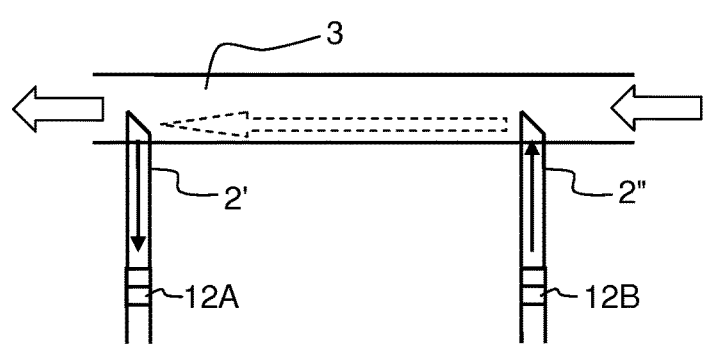

Embodiments of the present invention also address the risk that the operator of the machine 1 inadvertently confuses the access devices 2',2" when connecting them to the vascular access 3 or when connecting them to the connectors 12A, 12B (if present). FIGS. 2A-2B schematically illustrate a vascular access 3 and access devices 2',2" in a normal configuration and a reversed configuration, respectively. The blood flow in the vascular access 3 and access devices 2',2" are indicated by arrows. As seen, blood flows in a given direction through the vascular access 3. In the normal configuration of FIG. 2A, the access device 2' for blood withdrawal is positioned at an upstream portion for extracting blood and the access device 2" for blood return is positioned at a downstream portion for returning blood to the vascular access 3. In the reversed configuration of FIG. 2B, the access device 2' is positioned at the downstream position and the access device 2" is positioned at the upstream position, with the consequence of treated blood being returned upstream and being extracted downstream. In the reversed configuration, some of the already treated blood is again withdrawn into the EC circuit 1a, as phenomenon commonly known as recirculation and indicated by a dashed arrow in FIG. 2B. By the recirculation, less blood flowing from the body into the vascular access 3 will be treated, leading to reduced treatment efficiency. It is realized that the reversed configuration in FIG. 2B may also arise if the connectors 12A, 12B are confused, leading to a situation in which the access device 2' for blood withdrawal effectively is converted into an access device 2" for blood return, and vice versa. As is well-known to the skilled person, recirculation may occur even with access devices 2',2" in the normal configuration, if the blood flow rate in the EC circuit 1a exceeds the incoming blood flow rate to the vascular access 3. This situation will be discussed in more detail in relation to FIG. 6A below.

Although the access device 2',2" are illustrated in FIGS. 2A-2B as needles that puncture the skin to gain access to the patient's blood supply, a reversed placement may occur with other types of access devices as well. For example, the access devices 2',2" may be implemented as a double lumen catheter (not shown) which comprises two parallel channels which terminate at a distance from each other. One lumen is configured to remove blood for treatment, and the other lumen to return the treated blood. Like in FIG. 2B, a reversed configuration occurs if the double lumen catheter is inserted in a reversed direction into the vascular access or if the double lumen is incorrectly connected to the bloodlines.

Embodiments of the invention enable automatic verification before a treatment session that the dialyzer 4 is properly installed in the machine 1, and that the access devices 2',2" are properly connected to the patient. Embodiments of the invention also enable signaling of connection errors resulting in a co-current configuration of the dialyzer and/or a reversed configuration of the access devices 2',2".

Figure 3:
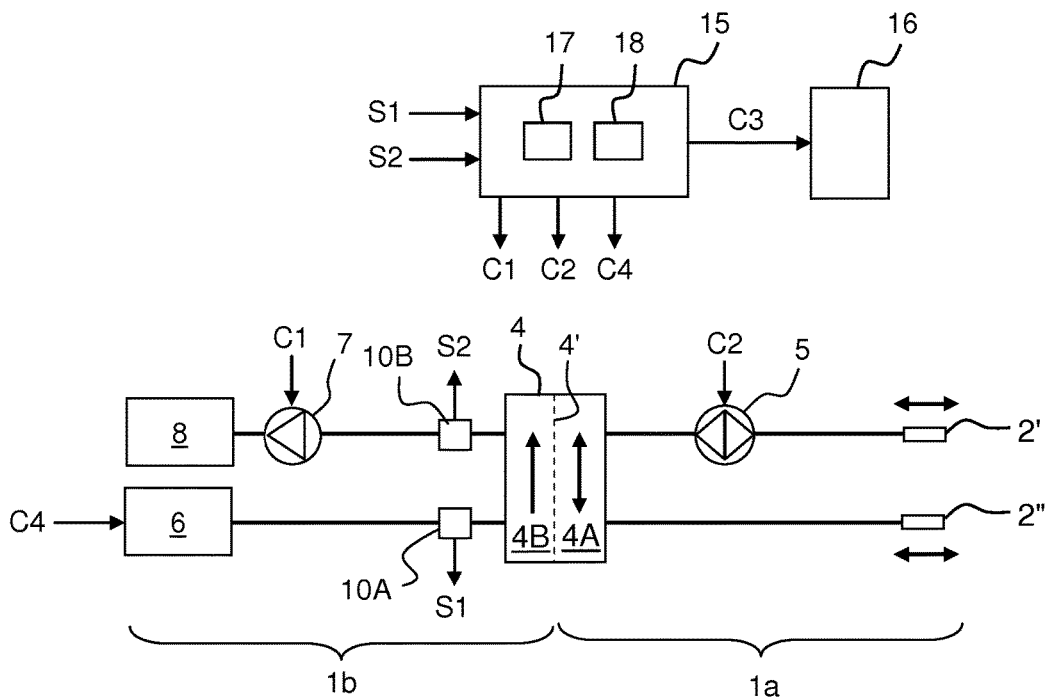
FIG. 3 is a block diagram of a dialysis system with a control unit.

FIG. 3 illustrates an embodiment of the invention that comprises a control unit 15 (also denoted control device or controller) which is configured to control the operation of the machine 1 in FIG. 1, at least during a test phase aiming to detect connection errors and, if needed, take corrective action. The control unit 15 comprises a signal interface for input and output of signals. Specifically, the control unit 15 is configured to generate and output control signals C1, C2, C4 for the treatment fluid pump 7, the blood pump 5, and the source 6 of treatment fluid, and to receive and process measurement signals S1, S2 from sensors 10A, 10B arranged in the TF circuit 1b, on both sides of the treatment fluid chamber 4B. The control unit 15 is also connected, by wire or wirelessly, to a user interface (UI) device 16 for interacting with the operator of the machine 1. The control unit 15 is configured to generate and output a control signal C3 for operating the UI device 16, e.g. to generate warning or alarm signals (audible and/or visible), display messages with information or instructions for the operator, graphically indicate the location of connection errors, etc. The UI device 16 may also be operable by the control unit 15 to receive input from the operator. The UI device 16 may thus comprise one or more of a display, a touch panel, a loudspeaker, a microphone, a keyboard, a mouse, an indicator lamp, etc. It is understood that the UI device 16 may be (part of) a conventional user interface on the machine 1.

The operation of the control unit 15 may be at least partly controlled by software instructions that are supplied on a computer-readable medium for execution by a processor 17 in conjunction with an electronic memory 18 in the control unit 15. In particular, the control unit 15 is configured to, by control signal C2, control the blood pump 5 to either operate in a default, forward direction and a reverse direction. The control signal C2 may also set the speed of the blood pump 5 and thus the flow rate of blood in the EC circuit 1a. By control signal C1, the control unit 15 sets the speed of the treatment fluid pump 7 and thus the flow rate of treatment fluid through the dialyzer 4. By control signal C4, the control unit 15 may set the temperature and/or composition of the treatment fluid provided by the source 6. As indicated by double-ended arrows in the dialyzer 4 and adjacent to the access devices 2',2", a switching of the blood pump 5 between the forward and reverse directions causes a simultaneous change of the flow direction in the blood compartment 4A and through the access devices 2',2". Thus, by switching the pumping direction of the blood pump 5, the machine 1 is switched between first and second operating states, which differ by the flow directions in the blood chamber 4A and through the access devices 2',2".

Figure 4A:
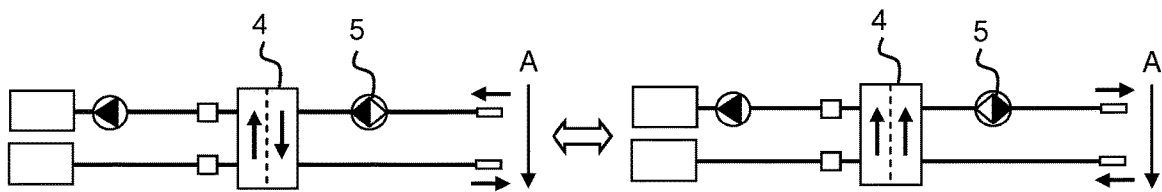
FIGS. 4A-4D illustrate possible flow direction statuses obtained by switching the direction of the blood pump in FIG. 3 from normal to reverse.
Figure 4B:
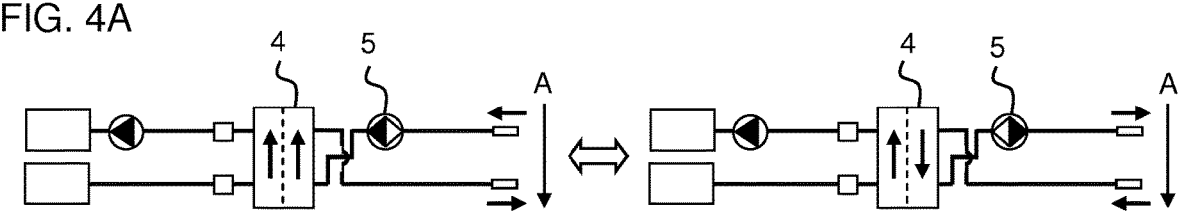
Figure 4C:
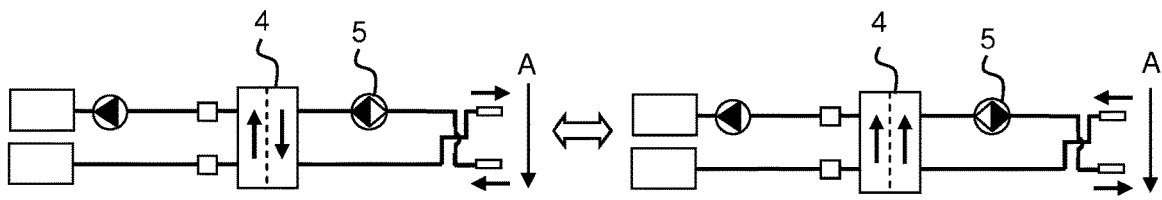
Figure 4D:
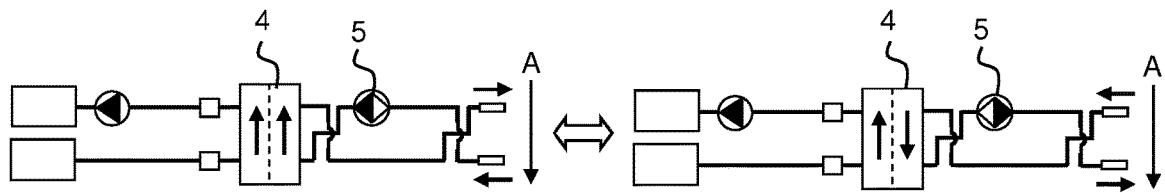
Figure 5:
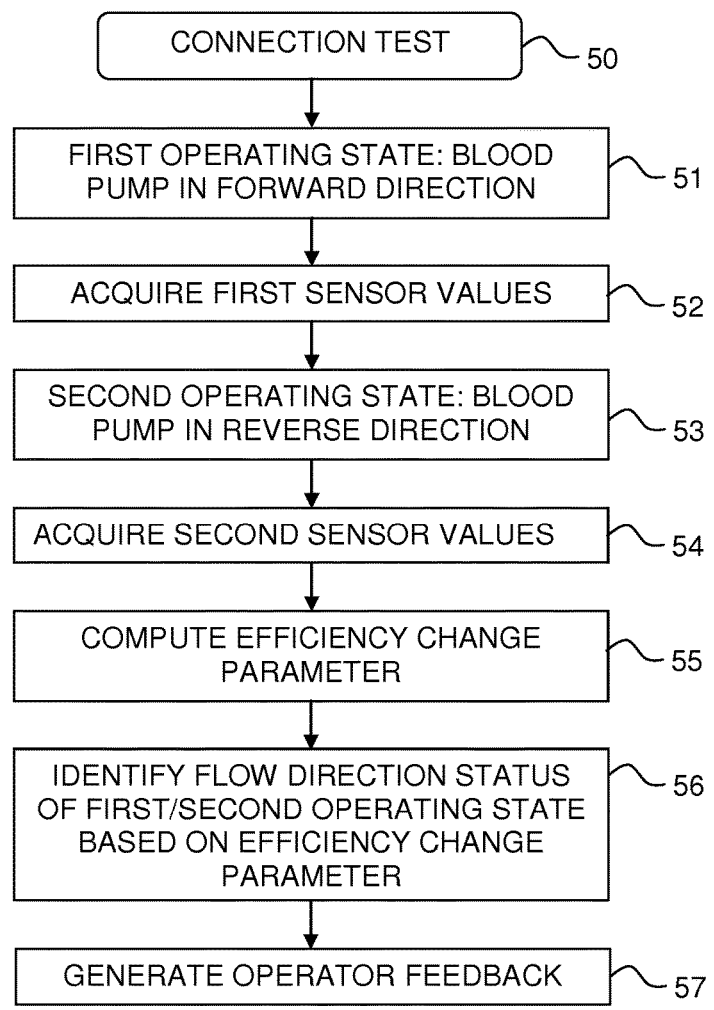
FIG. 5 is a flow chart of a method implemented by the control unit in FIG. 3.

FIGS. 4A-4D illustrate four possible switches between flow direction statuses of the machine 1 in FIG. 5, depending on how connections are made to the dialyzer 4 and to the vascular access 3. The arrow A indicates the direction of the access flow, i.e. the flow of blood into the vascular access 3 from the cardiovascular system of the subject. The pumping direction of the blood pump 5 is indicated by a filled triangle. In FIG. 4A, the machine 1 is switched between a first operating state in "correct condition" (left), i.e. with counter-current configuration of the dialyzer 4 and normal configuration of the access devices 2',2", and a second operating state in "dual fault condition" (right), i.e. with co-current configuration of the dialyzer 4 and reversed configuration of the access devices 2',2". In FIG. 4B, the machine 1 is switched between a first operating state in "dialyzer fault condition" (left), i.e. with co-current configuration of the dialyzer 4 and normal configuration of the access devices 2',2", and a second operating state in "access fault condition" (right), i.e. with counter-current configuration of the dialyzer 4 and reversed configuration of the access devices 2',2". In FIG. 4C, the machine 1 is switched between a first operating state in the access fault condition and a second operating state in the dialyzer fault condition. In FIG. 4D, the machine 1 is switched between a first operating state in the dual fault condition and a second operating state in the correct condition. Although FIGS. 4B-4D illustrate erroneous connections to the dialyzer 4 in the EC circuit 1a, it is to be understood that erroneous connections the dialyzer 4 may instead, or additionally, be made in the TF circuit 1b. In these cases, the machine 1 will also be switched from either the correct condition to the dual fault condition, or vice versa, or from the dialyzer fault condition to the access fault condition, or vice versa. Thus, FIGS. 4A-4D represent all possible switches between flow direction statuses for the machine 1 in FIG. 1, based on a reversal of the blood pump 5.

The control unit 15 is configured to perform a connection test, which involves switching the pumping direction of the blood pump 5, to verify that both the dialyzer 4 and the access devices 2',2" are correctly connected. FIG. 5 is a flow chart of a method executed by the control unit 15 during such a connection test 50 according to one embodiment. During this connection test 50, the machine 1 is switched between a first operating state and a second operating state, e.g. according to FIGS. 4A-4D. When executing this switch, the control unit 15 has no a priori information about the flow directions in the dialyzer 4 or through the access devices 2',2", but is rather configured to infer this information based on readings from the sensors 10A, 10B. In step 51, the control unit 15 generates control signals C1, C2 to set the machine 1 in the first operating state. Specifically, the blood pump 5 is controlled to operate in a default direction, which is also denoted "forward direction" herein. The default direction is predefined for the blood pump 5 so as to generate a desired flow direction through the EC circuit 1a. While the machine 1 is in the first operating state, the control unit 15 acquires first sensor values from the sensors 10A, 10B (step 52). In step 53, the control unit 15 generates control signals C1, C2 to set the machine 1 in a second operating state, inter alia by controlling the blood pump 5 to operate in a reverse direction. While the machine 1 is in the second operating state, the control unit 15 acquires second sensor values from the sensors 10A, 10B (step 54). In step 55, an efficiency change parameter is calculated as a function of the first and second sensor values to represent the change in in-vivo clearance associated with the switch of pumping direction between steps 51 and 53. The connection test 50 is then implemented to discriminate between different flow direction statuses of the machine 1 based on the efficiency change parameter. In step 56, the efficiency change parameter is evaluated to determine if the machine 1 has been switched between the correct condition and the dual fault condition, e.g. according to FIG. 4A or FIG. 4D, or between the dialyzer fault condition and the access fault condition, e.g. according to FIG. 4B or FIG. 4C. As will be further exemplified with reference to FIGS. 9-10, step 56 may compare the efficiency change parameter to predefined limits or ranges to discriminate between different flow direction statuses and detect connection errors in the first operating state. Depending on implementation, step 56 may result in different levels of detail regarding the connection errors. In a first example, the control unit 15 is configured to discriminate between all of the different flow direction statuses in FIGS. 4A-4D and thus determines if the first operating state is in the correct condition, the dual fault condition, the access fault condition or the dialyzer fault condition. In a second example, the control unit 15 is configured to determine if the first operating state is in the correct condition, the dual fault condition or a "single fault condition" (i.e. in any of the access fault condition and the dialyzer fault condition). In both of the first and second examples, the control unit 15 may additionally determine a "potential fault condition", which deemed to potentially involve a fault condition.

In step 57, the control unit 15 may generate feedback to the operator of the machine 1 based on the outcome of step 56, by controlling the UI device 16 via the control signal C3. In one example, if the first operating state is found to be in the dual fault condition, the single fault condition, the access fault condition or the dialyzer fault condition, the feedback may indicate to the operator that the connection test has failed. In another example, if the first operating state is found to be in the dual fault condition, the feedback may explicitly or implicitly instruct the operator to change the connection of the dialyzer 4 and the connection of the access devices 2',2". Alternatively, if the first operating state is found to be in the dual fault condition, the control unit 15 may automatically correct the error by operating the blood pump 5 in the reverse direction during blood treatment. In another example, if the first operating state is found to be in the correct condition or, equivalently, if the second operating state is found to be in the dual fault condition, the feedback may confirm to the operator that the machine 1 is correctly connected. Alternatively or additionally, the control unit 15 may be configured to selectively enable the machine 1 to start a blood treatment session if the machine 1 passes the connection test 50. In yet another example, if the first operating state is found to be in the single fault condition, the feedback may explicitly or implicitly instruct the operator to check both the connection of the dialyzer 4 and the connection of the access devices 2',2". In yet another example, if the first operating state is found to be in the access fault condition, the feedback may explicitly or implicitly instruct the operator to change the connection of the access devices 2',2". In yet another example, if the first operating state is found to be in the dialyzer fault condition, the feedback may explicitly or implicitly instruct the operator to change the connection of the dialyzer 4. In still another example, if the first operating state is found to be in the potential fault condition, the feedback may inform the operator about a possible connection error and instruct the operator to check both the connection of the dialyzer 4 and the connection of the access devices 2',2". Alternatively or additionally, the feedback may instruct the operator to enter further data about the system, e.g. to identify the dialyzer 4 to the control unit 15 (see discussion in relation to FIGS. 9A-9B below). In all of the foregoing examples, whenever the connection test fails, the control unit 15 may be configured to block the machine 1 from initiating a treatment session until the connection error has been resolved, e.g. as verified by a further, subsequent connection test, or by the operator affirming via the UI device 16 that the connections have been checked and are correct.

The skilled person realizes that the connection test 50 in FIG. 5 may be modified so that the machine 1 is instead switched from the second operating state to the first operating state, by switching the blood pump 5 from the reverse direction to the forward direction.

It should also be understood that there are many alternatives for computing the efficiency change parameter in step 55, based on the measurements in steps 52, 54. Typically, the efficiency change parameter is computed based on efficiency values computed for the first operating state and the second operating state, respectively. The efficiency values are computed based on the measurement signals S1, S2 to be indicative of, and typically proportional to, the in-vivo clearance in the respective operating state.

In one example, the control unit 15 implements an established technique for on-line monitoring in-vivo clearance based on measurement signals from the sensors 10A, 10B, e.g. as presented in U.S. Pat. Nos. 5,024,756, 5,100,554, EP0658352 and U.S. Pat. No. 6,702,774, and as used in above-mentioned WO2012/016671 (which are all incorporated herein by reference). This technique, in its different variants, is denoted "bolus technique" in the following and is characterized by involving the generation of a short-term bolus in concentration or temperature of the treatment fluid that is fed to the dialyzer 4. According to the bolus technique, the control unit 15 operates the TF circuit 1b, e.g. the source 6, to generate a short-term bolus (increase or decrease) in concentration of a dedicated marker substance or temperature. The marker substance may be any substance that is present in the blood and is capable of exchanging across the semi-permeable membrane 4', such as urea, creatinine, vitamin B12, beta-two-microglobulin, NaCl, or any ion or combination of ions. The sensors 10A, 10B may be dedicated concentration sensors capable of measuring the concentration of the marker substance. Alternatively, the sensors 10A, 10B may be conductivity sensors, which are responsive to ions in the treatment fluid, or temperature sensors. In practice, conductivity sensors will effectively indicate the concentration of ionized sodium in the treatment fluid. In another alternative, the sensors 10A, 10B may be absorbance sensors configured to determine optical absorbance as a measure of concentration. In still another alternative, the sensors 10A, 10B may be polarimetry sensors configured to determine polarization as a measure of concentration of an optically active substance, such as glucose, that rotates the plane of linearly polarized light. In still another alternative, the sensors 10A, 10B may be density sensors configured to measure the density (mass per unit volume) of the treatment fluid.

Thus, in step 52 and according to the bolus technique, the control unit 15 generates a short-term bolus and monitors the resulting change of the treatment fluid as measured by the sensors 10A, 10B ("first sensor values" in FIG. 5). The change is represented as a respective pulse in the measurement signals S1, S2. In one implementation, e.g. described in aforesaid U.S. Pat. Nos. 5,024,756, 5,100,554 and EP0658352, the control unit 15 determines measured values of the fluid property at the inlet and the outlet, respectively, of the treatment fluid chamber 4B of the dialyzer 4 at a first time point before the onset of the bolus and at a second time point corresponding to the peak of the bolus. The control unit 15 then computes the efficiency value as a function of these four measured values of the fluid property and the flow rate of treatment fluid during the bolus. In another implementation, e.g. described in aforesaid U.S. Pat. No. 6,702,774 and WO2012/016671, the control unit 15 integrates the respective pulse, and computes the efficiency value as a function of the ratio of the integrated pulses and the flow rate of treatment fluid during the bolus. The same procedure is repeated in step 54.

While this is an established technique, it has its inherent drawbacks. First, the bolus generation induces a significant disturbance of the operation of the TF circuit 1b, which may require more advanced mechanisms for controlling its operation. Second, the technique is time-consuming, since even a short-term bolus results in a relatively long pulse at the sensor 10B, due to the exchange process in the dialyzer 4. It is also necessary to ensure that the bolus change in marker concentration or temperature of the treatment fluid lies within physiologically acceptable limits. In a variant of this technique, also proposed in aforesaid U.S. Pat. No. 6,702,774, the bolus is generated by separately injecting a substance into the treatment fluid upstream of the dialyzer 4 and the sensor 10A.

As will be described further below with reference to FIGS. 6A-6C, it is possible to obtain the clearance parameters as a function of the measurement signals S1, S2 without generating a bolus, provided that certain operating conditions are fulfilled. This technique, which is denoted "non-bolus detection" herein, offers significant advantages over the prior art, since disturbances of the TF circuit 1b are minimized and the detection time is shortened.

As a still further alternative, the control unit 15 may be configured to compute the clearance parameters from concurrent measurements of urea concentrations in the systemic venous blood and the treatment fluid, e.g. in accordance with any of the techniques disclosed in U.S. Pat. No. 7,896,831 and references cited therein. In such an alternative, the sensors 10A, 10B may be urea monitors.

Figure 6A:
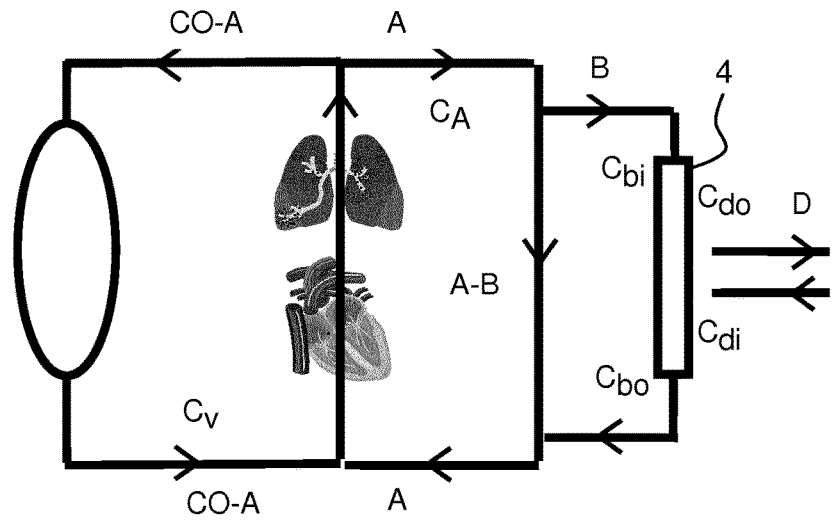
FIG. 6A is a hydraulic model of a patient connected to a dialysis system by access devices in a normal configuration, with counter-current flow in the dialyzer and without recirculation in the vascular access, FIG. 6B corresponds to FIG. 6A for a situation with recirculation in the vascular access, and FIG. 6C corresponds to FIG. 6A for a situation with the access devices in a reversed configuration.
Figure 6B:
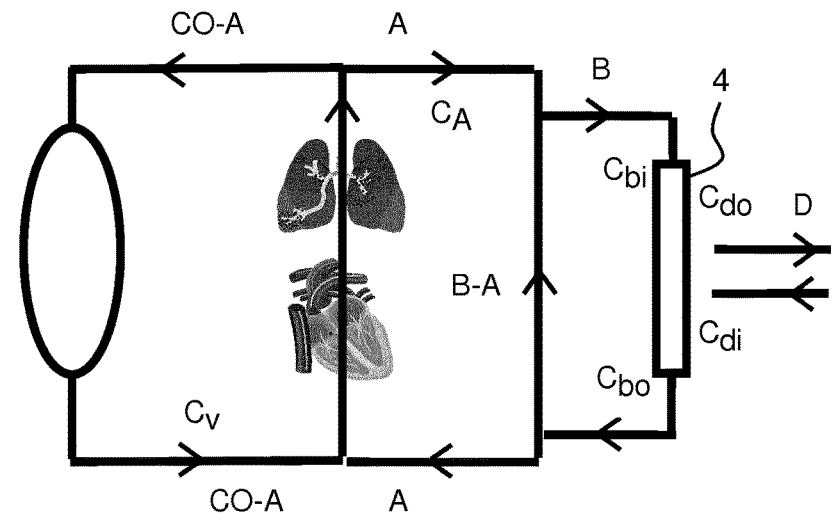
Figure 6C:
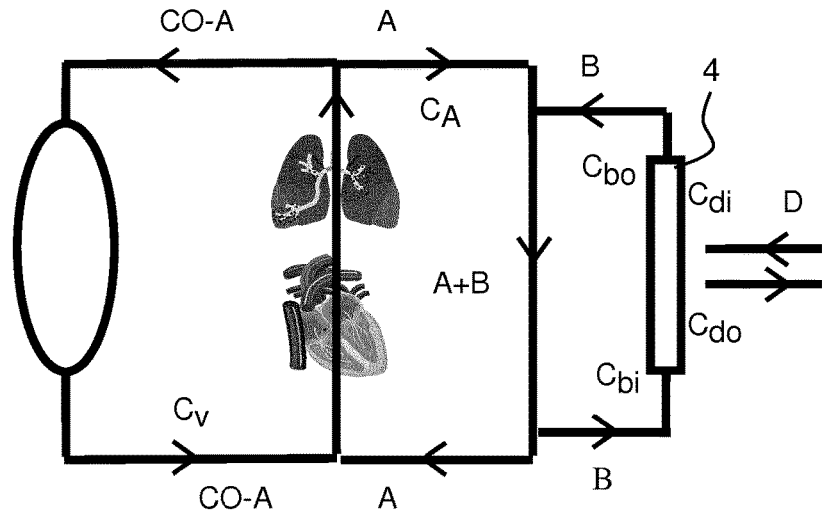

The non-bolus technique will now be further explained and motivated with reference to FIGS. 6A-6C, which illustrate a hydraulic model of a patient connected to a dialysis system for three different flow conditions in the vascular access. The aim of the following formal analysis of the hydraulic model is to derive expressions that represent the in-vivo clearance when the machine 1 in FIG. 3 is in each of the above-described flow direction statuses: correct condition, dialyzer fault condition, access fault condition and dual fault condition (cf. FIGS. 4A-4D). The formal analysis considers both large and small access flow rates, to account for recirculation within the vascular access 3 also when the access devices 2',2" are in the normal (correct) position. Although the following description refers to conductivity and conductivity sensors, it is equally applicable to other sensors, as explained above. Further, while the analysis assumes that the ultrafiltration rate is zero, the conclusions are sufficiently correct also in the presence of ultrafiltration. All flow rates below refer to blood water, which typically represents 85-90% of the total blood volume.

The following notation is used:
CO Cardiac Output (water flow rate)
A Access blood water flow rate
B Blood water flow rate to dialyzer
D Treatment fluid flow rate to dialyzer
$k_0A$ Mass transfer area coefficient of dialyzer (water value)
K Dialyzer clearance
$C_{bi}$ Blood water conductivity at dialyzer inlet
$C_{bo}$ Blood water conductivity at dialyzer outlet
α Donnan factor
$C_A$ Blood water conductivity in blood access
$C_v$ Blood water conductivity in venous blood from body
$C_{di}$ Treatment fluid conductivity at dialyzer inlet
$C_{do}$ Treatment fluid conductivity at dialyzer outlet For simplicity, the ultrafiltration rate is assumed to be zero. In this case, the dialyzer clearance K in the counter-current configuration is:

$$K = \frac{B \cdot D \cdot (1-f)}{D - f \cdot B} \quad (1)$$

with $$f = \exp(k_0 A \cdot (1/D - 1/B)) \quad (2)$$

In the co-current configuration, the dialyzer clearance K is $$K = \frac{B \cdot D \cdot (1-f)}{B + D} \quad (3)$$

with $$f = \exp(-k_0 A \cdot (1/D + 1/B)) \quad (4)$$

The transport from blood to treatment fluid can be expressed in three ways, looking at what leaves the blood side, enters the dialysis fluid side or crosses the membrane, respectively:

$$B \cdot (C_{bi} - C_{bo}) = D \cdot (C_{do} - C_{di}) = K \cdot (\alpha \cdot C_{bi} - C_{di}) \quad (5)$$

These expressions are independent of the flow direction status of the dialyzer as long as the correct value for clearance is used (counter-current or co-current). Eq. (5) provides an expression for the conductivity difference ΔC in the treatment fluid:

$$\Delta C = C_{do} - C_{di} = \frac{K}{D} \cdot (\alpha \cdot C_{bi} - C_{di}) \quad (6)$$

It is important to note that K designates the dialyzer clearance, not the in-vivo clearance. The following formal analysis will show that the conductivity difference ΔC is not only directly proportional to the dialyzer clearance K, as indicated by Eq. (6), but also to the in-vivo clearance. The formal analysis aims at expressing Eq. (6) as a function of $C_v$, which may be considered invariant during the switch of pumping direction, instead of $C_{bi}$, which is affected by recirculation in the blood vessel access.

A first part of the formal analysis is based on FIG. 6A, which illustrates fluid flows in the hydraulic model with the access devices in the normal position and with an access flow rate that exceeds the blood water flow rate in the EC circuit (i.e. A>B). In this case, $C_{bi}$ is equal to $C_A$. A relation between $C_A$ and $C_v$ is given by a mass balance analysis at the joint before the heart-lung system, where the blood from the body with concentration $C_v$ is mixed with cleaned blood returning from the vascular access:

$$CO \cdot C_A = (CO-A) \cdot C_v + A \cdot C_A - D \cdot \Delta C \quad (7)$$

where the mass in the cleaned blood from the vascular access is calculated by subtracting the mass removed in the dialyzer (expressed as D·ΔC) from the mass going to the access from the heart. Eq. (7) is valid for all configurations and yields:

$$C_A = C_v - \frac{D}{CO - A} \cdot \Delta C \quad (8)$$

Inserting Eq. (8) into Eq. (6), with $C_A = C_{bi}$, and solving for ΔC yields:

$$\Delta C = \frac{1}{1 + \frac{\alpha \cdot K}{CO - A}} \cdot \frac{K}{D} \cdot (\alpha \cdot C_v - C_{di}) \quad (9)$$

with K being given by Eq. (1) or Eq. (3) above, depending on configuration (counter-current or co-current).

A second part of the formal analysis is based on FIG. 6B, which illustrates fluid flows in the hydraulic model with the access devices in the normal position but with an access flow rate that is lower than the blood water flow rate in the EC circuit (i.e. A<B). This means that part of the treated blood that is returned to the vascular access will be recirculated back into EC circuit. In this case, a mass balance analysis yields:

$$B \cdot C_{bi} = A \cdot C_A + (B-A) \cdot C_{bo} \quad (10)$$

$$B \cdot C_{bo} = B \cdot C_{bi} - D \cdot \Delta C \quad (11)$$

Combining Eq. (10), Eq. (11), Eq. (6) and Eq. (8) yields:

$$\Delta C = \frac{\beta}{1 + \beta \cdot \frac{\alpha \cdot K}{CO - A}} \cdot \frac{K}{D} \cdot (\alpha \cdot C_v - C_{di}) \text{ with} \quad (12)$$

$$\beta = \frac{A \cdot B}{A \cdot B + \alpha \cdot K \cdot (B - A)} \quad (13)$$

Eq. (9) and Eq. (12) may be summarized in one equation covering all values of A:

$$\Delta C = \min\left(\frac{1}{1 + 1 \cdot \frac{\alpha \cdot K}{CO - A}}, \frac{\beta}{1 + \beta \cdot \frac{\alpha \cdot K}{CO - A}}\right) \cdot \frac{K}{D} \cdot (\alpha \cdot C_v - C_{di}) \quad (14)$$

A third part of the formal analysis is based on FIG. 6C, which illustrates fluid flows in the hydraulic model with the access devices in reversed position. In this case, a mass balance analysis yields:

$$A \cdot C_{bi} = A \cdot C_A - D \cdot \Delta C \quad (15)$$

Combining Eq. (15), Eq. (6) and Eq. (8) yields:

$$\Delta C = \frac{A \cdot (CO - A)}{A \cdot (CO - A) + \alpha \cdot K \cdot CO} \cdot \frac{K}{D} \cdot (\alpha \cdot C_v - C_{di}) \quad (16)$$

Both Eq. (14) and Eq. (16) may be rewritten as:

$$\Delta C = \frac{K_{eff}}{D} \cdot (\alpha \cdot C_v - C_{di}) \quad (17)$$

where $K_{eff}$ is the in-vivo clearance ("effective clearance"). Eq. (17) shows that changes in the conductivity difference $\Delta C$ may be used to analyze changes in the in-vivo clearance $K_{eff}$, provided that the dialysis fluid flow rate D, the inlet conductivity $C_{di}$, the Donnan factor $\alpha$, and the blood concentration $C_v$ are unchanged. The Donnan factor $\alpha$ may be regarded as a constant; in practice it is always close to 1, and any change will be very small and have a minute impact on the result. Further, as noted above, neither a reversal of the blood pump 5, nor a possible change of the blood flow rate B, will affect $C_v$. However, it should be noted that the in-vivo clearance $K_{eff}$ is affected by the blood flow rate B, see e.g. Equations (1), (3) and (13). Thus, to the extent that the conductivity difference $\Delta C$ is used to analyze the effect of a switch of pumping direction, the blood flow rate B should remain essentially invariant during the change. In summary, the foregoing analysis indicates that the non-bolus technique is applicable for use in the connection test 50, provided that each of the following operational parameters is controlled to be essentially unchanged during and between steps 52 and 54: the blood flow rate B, the treatment fluid flow rate D and the conductivity $C_{di}$ of treatment fluid at the inlet to the dialyzer 4. In this context, "essentially unchanged" means that slight variations in the respective operational parameter are allowed to the extent that the resulting change in $\Delta C$ is small compared to the change caused by the switch of pumping direction. Typically, a $\Delta C$ change of 1%, ±2%, ±5% or ±10% caused by variations in these operational parameters is deemed small. For example, the blood flow rate B generated by the blood pump 5 may differ slightly between the pumping directions, even if the speed of the blood pump is maintained invariant, since the switch of pumping direction may change the fluid pressure at the inlet of the pump. Resulting differences in blood flow rate B may be reduced, if deemed necessary, by implementing well-known compensation techniques, e.g. as disclosed in U.S. Pat. No. 4,468,219, which adjust the speed of the pump based on measured fluid pressure upstream of the pump. Thus, in the context of FIG. 3, the control unit 15, or a dedicated pump controller (not shown), may be configured to adjust the control signal C2 for the blood pump 5 based on a pressure signal from a pressure sensor (not shown) located in the EC circuit 1a upstream of the blood pump 5 in the first or second operating state, so that the control signal C2 causes the blood pump 5 to maintain an essentially unchanged blood flow rate B in the first and second operating states. It is also conceivable to apply the compensation technique based on pressure signals from pressure sensors on both sides of the blood pump 5.

Reverting now to the connection test 50 in FIG. 5, step 52 may involve acquiring a respective first sensor value from the sensors 10A, 10B, step 54 may involve acquiring a respective second sensor value from the sensors 10A, 10B, and step 55 may involve computing a $\Delta C$ value for the first operating state and the second operating state, respectively. For the purpose of comparing the in-vivo clearance between the first and second operation states, based on the $\Delta C$ values, the parameters B, D and $C_{di}$ are controlled to be essentially unchanged between and during steps 52 and 54. In step 55, the efficiency change parameter is computed as a function of the $\Delta C$ values so as to represent the change in in-vivo clearance.

It is important to note that the measurements of the conductivity difference $\Delta C$ before and after the blood pump reversal are made without changing the inlet conductivity $C_{di}$, and thus without generating any bolus in the TF circuit 1b. It should be noted that the switch of pumping direction will not cause a change in measured conductivity difference $\Delta C$ if the inlet conductivity is equal to the plasma conductivity of the patient, i.e. $C_{di} = \alpha \cdot C_v$ in Eq. (17). Thus, it may be preferable, before initiating the connection test 50, to verify that the measured conductivity difference $\Delta C$ exceeds a minimum value, which may be predefined to yield a sufficient accuracy of the connection test 50. For example, the control unit 15 may operate the machine 1 in the first or second operating state, using predefined values of B, D and $C_{di}$, compute a $\Delta C$ value based on the measurements signals S1, S2 and compare the $\Delta C$ value to the minimum value. If the $\Delta C$ value is less than the minimum value, the control unit 15 operates the source 6, by generating the control signal C4, to adjust the inlet conductivity $C_{di}$ so that the $\Delta C$ value exceeds the minimum value. It is conceivable that this adjustment is made for $\Delta C$ values computed for both the first operating state and the second operating state. The verification is a preparatory procedure, which is completed in advance of the connection test 50 in FIG. 5. The connection test 50 is then conducted with the predefined values of B, D and with the inlet conductivity $C_{di}$ given by the verification.

It should also be understood that the upstream sensor 10A may be omitted if the inlet conductivity $C_{di}$ is otherwise known to the control unit 15, e.g. from the settings of the TF circuit 1b (e.g. via control signal C4).

The evaluation in step 56 of FIG. 5 is implemented based on an understanding of how the conductivity difference $\Delta C$ changes depending on the flow direction status of the first operating state. This understanding will be further explained and exemplified based on Eq. (14) and Eq. (16), with K taken from Eq. (1) for a counter-current dialyzer configuration and from Eq. (3) for a co-current dialyzer configuration.

Figure 7:
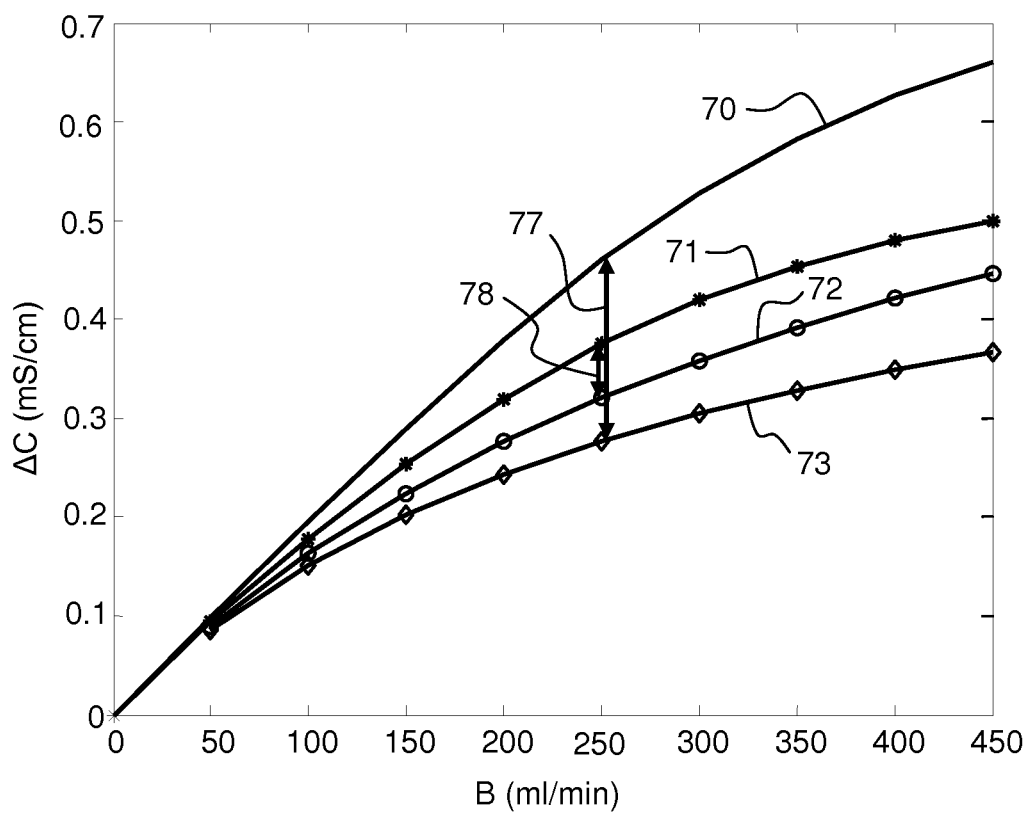
FIG. 7 is plot of calculated conductivity differences obtained over the dialyzer for different flow direction statuses of the dialysis system in FIG. 3, as function of blood flow rate in the EC circuit.

FIG. 7 is a plot of theoretically calculated values of $\Delta C$ as a function of blood flow rate B for various flow direction statuses of the machine 1 in FIG. 3. Curve 70 is calculated for a counter-current dialyzer configuration and a normal access device configuration (i.e. the correct condition). Curve 71 is calculated for a counter-current dialyzer configuration and a reversed access device configuration (i.e. the access fault condition). Curve 72 is calculated for a co-current dialyzer configuration and a normal access device configuration (i.e. the dialyzer fault condition). Curve 73 is calculated for a co-current dialyzer configuration and a reversed access device configuration (i.e. the dual fault condition). Curves 70-73 are calculated for a conductivity gradient between blood and treatment fluid of 1 mS/cm, CO=5 l/min, D=500 ml/min, $k_0A$=1500 ml/min, A=1000 ml/min, and no ultrafiltration.

FIG. 7 indicates that there is a considerable difference in ΔC values between the different flow direction statuses. Arrow 77 indicates the change in ΔC value when switching, at a blood flow rate B=250 ml/min, from the correct condition to the dual fault condition, or vice versa (cf. FIG. 4A and FIG. 4D), and arrow 78 indicates the change in ΔC value when switching from the access fault condition to the dialyzer fault condition, or vice versa (cf. FIG. 4B and FIG. 4C). As seen, the change 77 is much larger than the change 78. Thus, it is possible to discriminate between a switch between the correct condition and the dual fault condition, and a switch between the access fault condition and the dialyzer fault condition. Further, since the curves 70-73 are well-separated, it is possible to use the sign of the change to allocate a flow direction status to the first and second operating states, at least for blood flow rates B of about 100 ml/min or larger.

The skilled person readily realizes that there are numerous ways of formalizing the foregoing analysis into computation and evaluation of an efficiency change parameter according to steps 55-56 in FIG. 5. In one example, the efficiency change parameter is computed as a (weighted) difference of the ΔC values in step 55, which may be analyzed with respect to magnitude and sign in step 56. In another example, the efficiency change parameter is given by or computed as a function of a ratio R of the ΔC values in step 55, which may be analyzed with respect to magnitude.

Although FIG. 7 indicates that it is indeed possible to perform the connection test so as to allocate a specific flow direction status to the first operating state, and thereby provide adequate feedback to the operator (step 57), it remains to determine if this allocation is possible for all values of the different controlling parameters that are included in the relevant equations. The controlling parameters include both operational parameters, which are known to and may be set by the control unit 15, and system parameters, which cannot be modified by the control unit 15. The operational parameters are the blood flow rate B and the treatment fluid flow rate D. The system parameters are the membrane permeability $k_0A$, the access flow rate A and the cardiac output CO. The membrane permeability $k_0A$ may be known to the control unit 15, e.g. if information about the installed dialyzer 4 is supplied to or acquired by the machine 1. However, the access flow rate A and the cardiac output CO are usually not known to the control unit 15, since they are unique to the patient and may also change over time. Thus, the connection test should preferably be independent of at least the access flow rate A and the cardiac output CO.

Figure 8A:
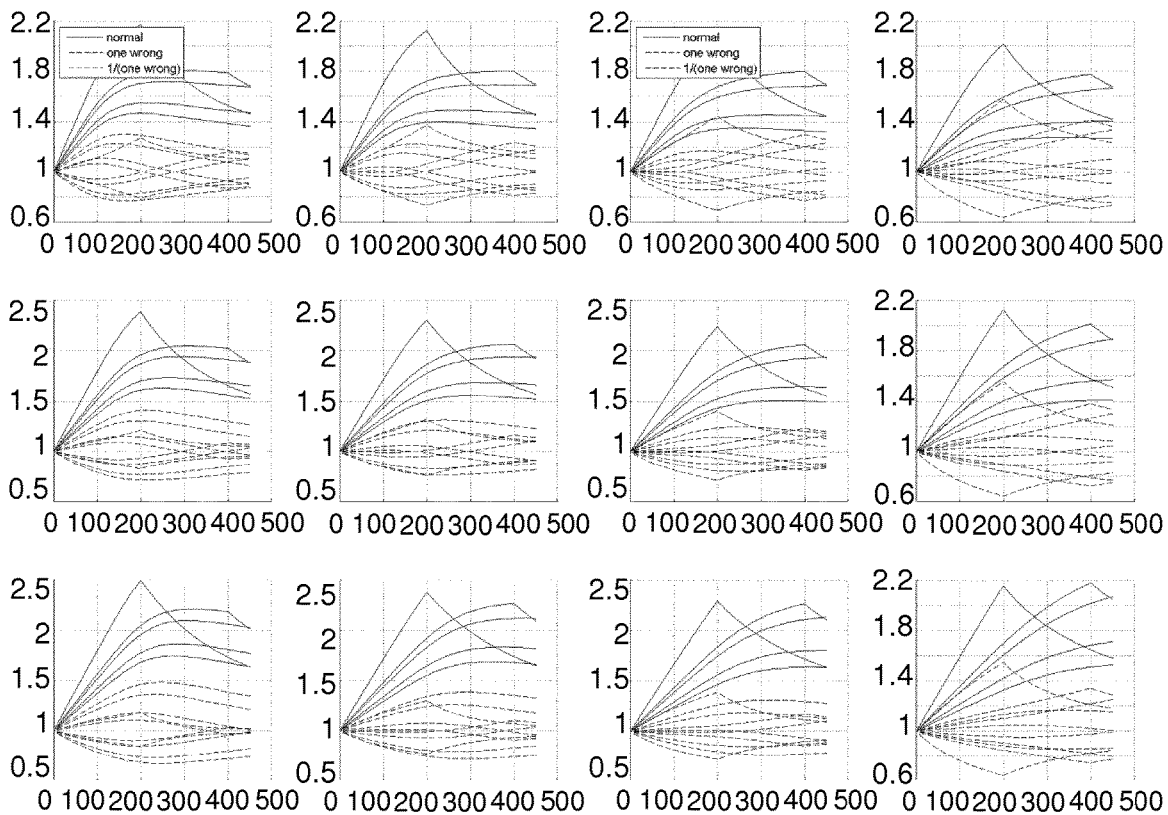
FIG. 8A comprises graphs that each illustrate calculated conductivity ratios as a function of blood flow rate for different flow direction statuses and access flows, for a cardiac output of 6 l/min, wherein the graphs are arranged with increasing dialysis fluid flow rate in the horizontal direction and increasing dialyzer membrane permeability in the vertical direction.
Figure 8B:
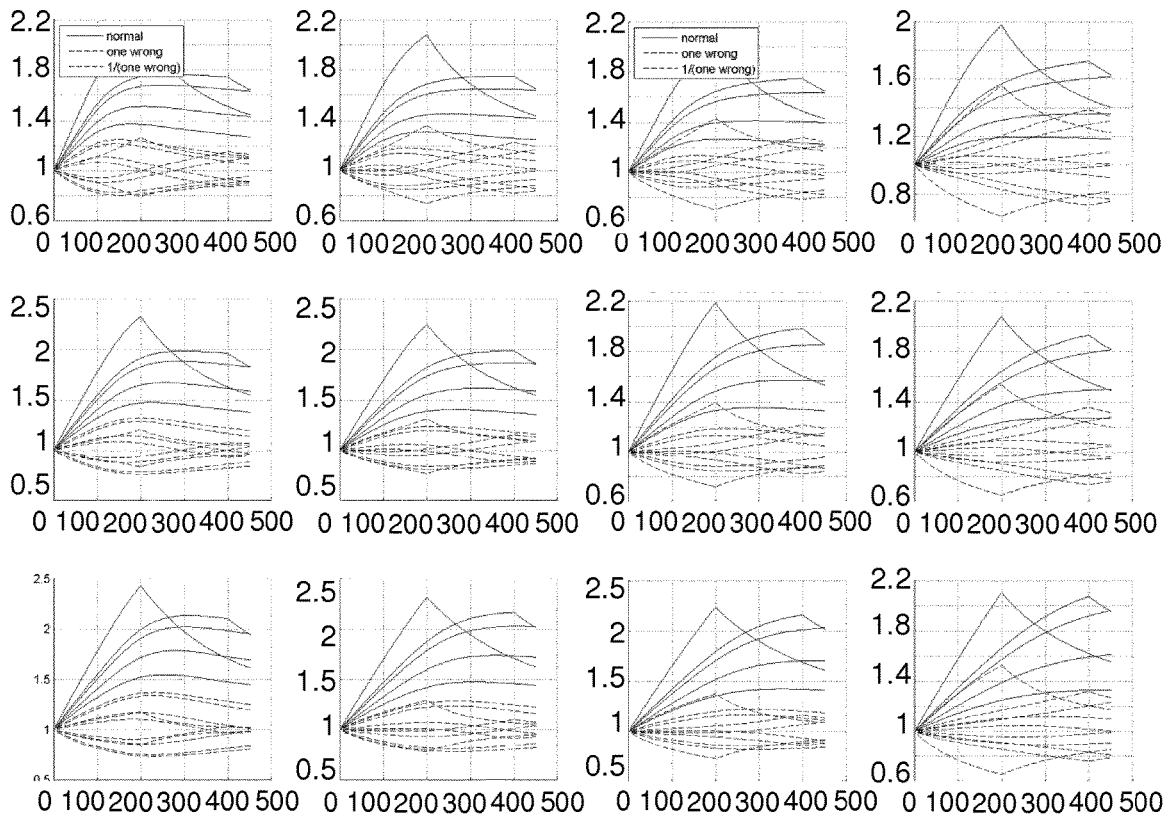
FIG. 8B illustrates corresponding graphs for a cardiac output of 2.5 l/min.

The limits of the connection test will be further examined with reference to simulation results presented in FIGS. 8A-8B. The simulations have been based on Equations (1), (3), (14) and (16) above. FIG. 8A is collation of a large number of graphs computed for CO=6 l/min and organized to represent increasing D in the horizontal direction (300 ml/min, 400 ml/min, 500 ml/min and 800 ml/min) and increasing $k_0A$ in the vertical direction (600 ml/min, 1000 ml/min and 1500 ml/min). Each individual graph illustrates curves for computed ratios R of ΔC values (before and after a switch) as a function of blood flow rate B for five different access flow rates A (200 ml/min, 400 ml/min, 500 ml/min, 1000 ml/min and 1500 ml/min). The ratios R are computed for three different switches: from the correct condition to the dual fault condition (solid lines), from the dialyzer fault condition to the access fault condition (dashed lines), and from the access fault condition to the dialyzer fault condition (dashed lines). FIG. 8B is a corresponding collation of graphs computed for CO=2.5 l/min.

The graphs in FIGS. 8A-8B indicate that it is possible, irrespective of A, CO and $k_0A$, to discriminate between the correct condition and the dual fault condition, since the ratio R when switching from the correct condition and to the dual fault condition (solid curves) is always greater than one (1). In order to discriminate between the correct condition (or equivalently, the dual fault condition) and a single fault condition (dashed curves), there should be a clear separation between the solid curves and the dashed curves in the graphs for all values of the access flow rate A and the cardiac output CO. As seen in FIGS. 8A-8B, there is an increased tendency for overlap between dashed and solid curves for high treatment fluid flow rates D, low blood flow rates B and small membrane permeability $k_0A$. Conversely, this means that it is possible ensure a clear separation between solid curves and dashed curves by proper selection of the treatment fluid flow rate D and the blood flow rate B. FIGS. 8A-8B indicate that the treatment fluid flow rate D should be minimized. At D=800 ml/min, there is considerable overlap of the solid curves and the dashed curves, which partly remains at D=500 ml/min, especially when CO=2.5 l/min. In one example, the treatment fluid flow rate D may be set in the range of 200-400 ml/min to minimize overlap. The blood flow rate B should not be too low and not too high. At low B, the separation will be small if the access flow rate A is so low that there is a risk for recirculation. This means that the blood flow rate B should be set to exceed the access flow rate A in the vast majority of patients while still yielding adequate separation between the dashed and solid curves. In one example, the blood flow rate B may be set in the range of 200-300 ml/min.

Thus, the control unit 15 may be configured to, before step 51 in FIG. 5, obtain dedicated settings for the connection test 50 and then set the machine 1 in the first and second operating state based on the dedicated settings. The settings may be stored in the memory 18 and may comprise set values for B and D to be applied during the connection test 50. The settings may also comprise a set value for the inlet conductivity $C_{di}$ of the treatment fluid.

Figure 9A:
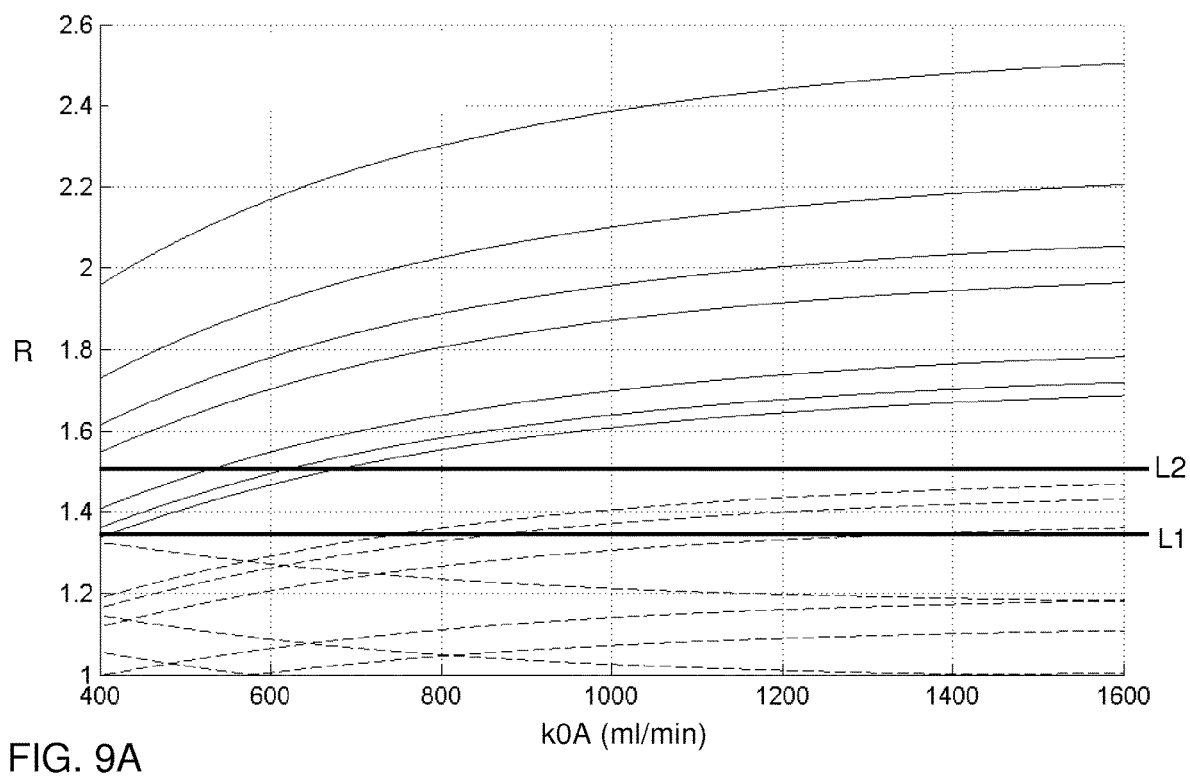
FIG. 9A is a graph of calculated conductivity difference ratios as a function of dialyzer membrane permeability for different flow direction statuses and access flows, for a given setting of the dialysis fluid flow rate and the blood flow rate, and for a cardiac output of 6 l/min.
Figure 9B:
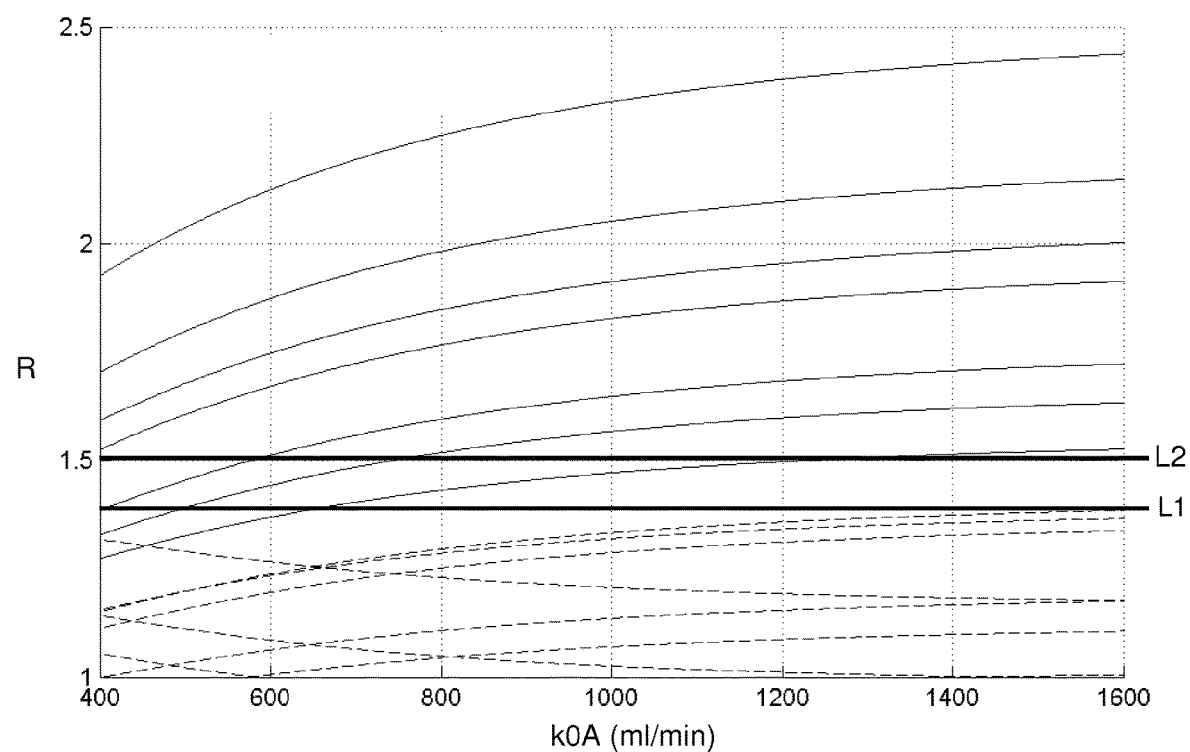
FIG. 9B illustrates a corresponding graph for a cardiac output of 2.5 l/min.

FIGS. 9A-9B illustrate further simulation results generated based on Equations (1), (3), (14) and (16) above, which may serve to further exemplify the evaluation in step 56. FIG. 9A is a plot of the calculated ratio R of ΔC values (before and after a switch) as a function of membrane permeability $k_0A$, at B=200 ml/min, D=300 ml/min and CO=6 l/min, for seven different access flow rates A (200 ml/min, 300 ml/min, 400 ml/min, 500 ml/min, 1000 ml/min, 1500 ml/min and 2000 ml/min). The solid curves represent a switch from the correct condition to the dual fault condition, and the dashed curves represent a switch between single fault conditions (from the dialyzer fault condition to the access fault condition, or vice versa). FIG. 9B is a corresponding plot computed for CO=2.5 l/min. It should be noted that the plots are given for R≥1, which means that certain dashed curves are not shown. It should also be noted that the two lowest solid curves in FIG. 9B correspond to access flow rates of 1500 ml/min and 2000 ml/min, which are unlikely to occur for a cardiac output of 2.5 l/min. Thus, the two lower solid curves in FIG. 9B are excluded from the following analysis for physiological reasons.

As seen from FIGS. 9A-9B, if the membrane permeability $k_0A$ of the installed dialyzer 4 is known, the solid curves and the dashed curves are separated for essentially all values of the membrane permeability $k_0A$. Thus, it is possible to set a limit as a function of the membrane permeability $k_0A$ that discriminates between the different switches. FIGS. 9A-9B also indicate that it is possible to discriminate between the different switches even if the membrane permeability $k_0A$ of the installed dialyzer 4 is unknown. This may be achieved by setting a first limit L1, in this example at R=1.35, below which there is certainly a connection error in the first operating state (i.e. either a single fault condition or a dual fault condition), and a second limit L2, in this example at R=1.5, above which the first operating state is certainly in the correct condition. Thus, in step 56, the control unit 15 may compare the R value, computed in step 55, to the limits L1, L2 and identify either a connection error if the R value falls below L1, a correct condition if the R value falls above L2, or a potential fault condition if the R value falls between the limits L1, L2. It should be noted, however, that the potential fault condition will only occur for dialyzers 4 with very small membrane permeability $k_0A$. In one implementation, the control unit 15 tries to resolve the potential fault condition by requesting the operator to enter data indicative of the membrane permeability $k_0A$ of the installed dialyzer 4, e.g. a model number or the like. Based on the entered data, the control unit 15 may retrieve a new limit, tailored to the membrane permeability $k_0A$ according to FIGS. 9A-9B, and apply the new limit in a second evaluation of the R value.

Figure 10A:
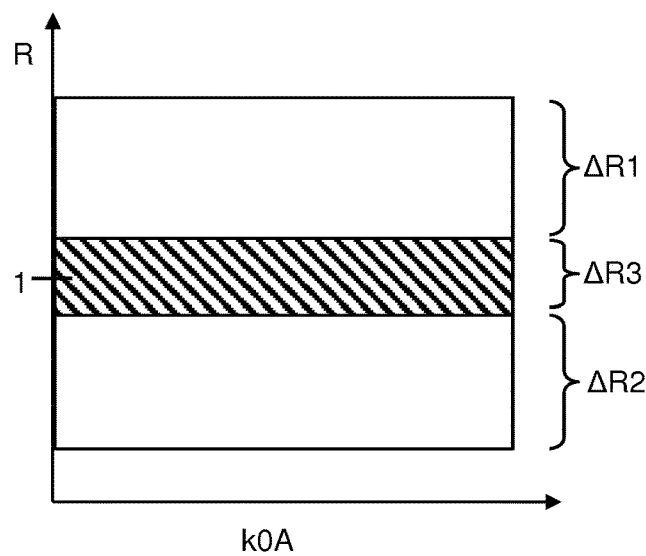
FIGS. 10A-10B show examples of ranges of conductivity difference ratios associated with the flow direction statuses shown in FIGS. 4A-4D and based on FIGS. 9A-9B.
Figure 10B:
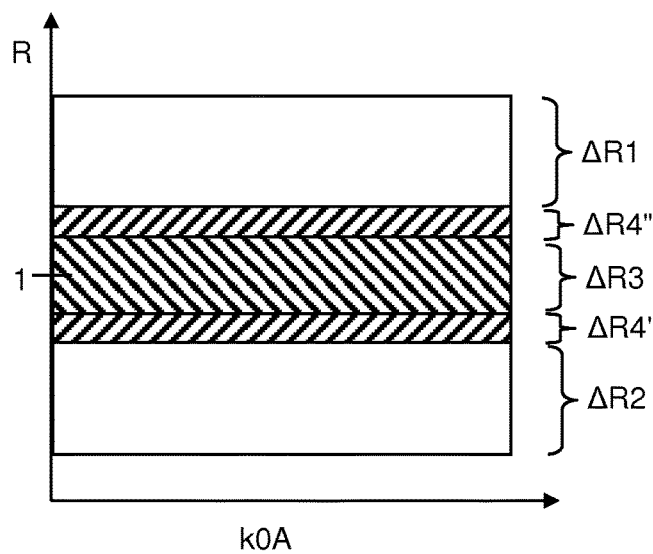
Figure 10C:
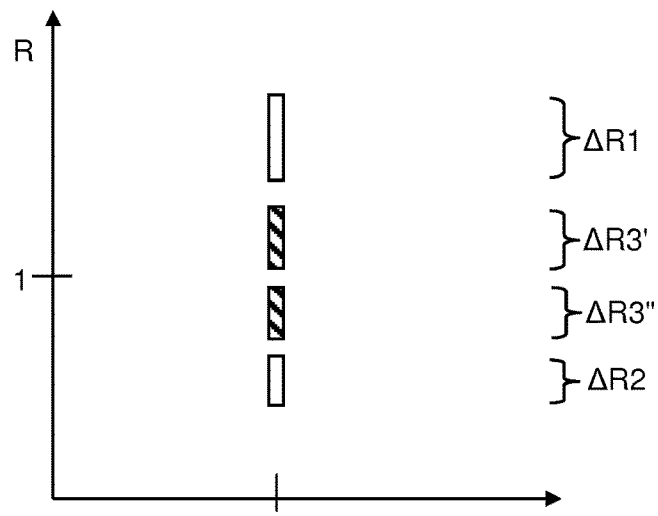
FIG. 10C shows an example of corresponding ranges defined based on FIG. 7.

FIGS. 10A-10C intend to summarize the foregoing discussion and illustrate different combinations of ranges that may be applied by the control unit 15 in step 56 of FIG. 5 when evaluating an R value computed in step 55. Each range is associated with a respective flow direction status of the machine 1 in the first operating state. Thus, in step 56, the control unit 15 may simply compare the R value to the different ranges to determine the flow direction status of the first operating state. The ranges may be identified to the control unit 15 by a range definition stored in the memory 18 (FIG. 3) for retrieval in step 56. The range definition may identify the respective range by an upper limit value and a lower limit value. It is also possible that one or more ranges are defined by either an upper limit value or a lower limit value, e.g. if the range is open-ended. Thus, as used herein, a "range" includes both closed and open-ended ranges. Depending on implementation, the range definition may be given for different combinations of operational and/or system parameters. Such a range definition may be implemented by one or more look-up tables and/or one or more functions for computing a respective range based on one or more current values of the operational and/or system parameters. Thus, in step 56, the control unit 15 may dynamically obtain the ranges by accessing the range definition based on current values of the operational and/or system parameters.

FIG. 10A illustrates ranges $\Delta R1$-$\Delta R3$ that are set to be applicable irrespective of the above-mentioned system parameters (A, CO, $k_0A$), where $\Delta R1$ corresponds to the correct condition, $\Delta R2$ corresponds to the dual fault condition, and $\Delta R3$ corresponds to the single fault condition. As understood from the foregoing discussion, the definition in FIG. 10A may only be valid if the machine 1 is operated within a predefined interval of blood flow rates B and/or treatment fluid flow rates D. The definition may even be limited to a specific combination of values for B and D. It should also be understood that a corresponding definition of $\Delta R1$-$\Delta R3$ may be used in step 56 even if one or more system parameters are known.

FIG. 10B illustrates variant of the definition in FIG. 10A, in which additional ranges $\Delta R4'$,$\Delta R4''$ are defined on both sides of $\Delta R3$, adjacent to $\Delta R2$ and $\Delta R1$, respectively. The ranges $\Delta R4'$,$\Delta R4''$ are both associated with the above-mentioned potential fault condition (cf. FIGS. 9A-9B).

FIG. 10C illustrates a range definition capable of identifying all possible flow direction statuses of the first operating state, where range $\Delta R1$ corresponds to the correct condition, $\Delta R2$ corresponds to the dual fault condition, $\Delta R3'$ corresponds to the access fault condition, and $\Delta R3''$ corresponds to the dialyzer fault condition. The range definition in FIG. 10C is typically valid for a specific combination of specific values or limited intervals of at least some of the operational parameters and system parameters. For example, the ranges may be defined based on FIG. 7, to be valid only for a specific combination of values/ranges of B, D, $k_0A$ and A, as indicated in FIG. 10C.

FIGS. 10A-10C also show that the detection technique proposed by WO2012/016671, discussed in the Background section, is unable to detect connection errors at the access devices 2',2", since it is exclusively configured to compare a ratio of clearance parameters to 1. In the terminology of the present disclosure, the technique in WO2012/016671 is designed to only discriminate between a correct condition (R>1) and a dialyzer fault condition (R<1), whereas embodiments of the invention are tailored to detect additional fault conditions, such as the dual fault condition (e.g. by $\Delta R2$), the single fault condition (e.g. by $\Delta R3$), the access fault condition (e.g. by $\Delta R3'$) and the potential fault condition (e.g. by $\Delta R4'$,$\Delta R4''$).

The control unit 15 as described herein may be implemented by special-purpose software (or firmware) run on one or more general-purpose or special-purpose computing devices. In this context, it is to be understood that an "element" or "means" of such a computing device refers to a conceptual equivalent of a method step; there is not always a one-to-one correspondence between elements/means and particular pieces of hardware or software routines. One piece of hardware sometimes comprises different means/elements. For example, a processor serves as one element/means when executing one instruction, but serves as another element/means when executing another instruction. In addition, one element/means may be implemented by one instruction in some cases, but by a plurality of instructions in some other cases. Such a software controlled computing device may include one or more processors (cf. 17 in FIG. 3), e.g. a CPU ("Central Processing Unit"), a DSP ("Digital Signal Processor"), an ASIC ("Application-Specific Integrated Circuit"), discrete analog and/or digital components, or some other programmable logical device, such as an FPGA ("Field Programmable Gate Array"). The control unit 15 may further include a system memory and a system bus that couples various system components including the system memory (cf. 18 in FIG. 3) to the processor. The system bus may be any of several types of bus structures including a memory bus or memory controller, a peripheral bus, and a local bus using any of a variety of bus architectures. The system memory may include computer storage media in the form of volatile and/or non-volatile memory such as read only memory (ROM), random access memory (RAM) and flash memory. The special-purpose software may be stored in the system memory, or on other removable/non-removable volatile/non-volatile computer storage media which is included in or accessible to the computing device, such as magnetic media, optical media, flash memory cards, digital tape, solid state RAM, solid state ROM, etc. The control unit 15 may include one or more communication interfaces, such as a serial interface, a parallel interface, a USB interface, a wireless interface, a network adapter, etc, as well as one or more data acquisition devices, such as an A/D converter. The special-purpose software may be provided to the control unit 15 on any suitable computer-readable medium, transitory or non-transitory, including a record medium or a read-only memory. It is also conceivable that some (or all) elements/ means are fully or partially implemented by dedicated hardware, such as an FPGA, an ASIC, or an assembly of discrete electronic components (resistors, capacitors, operational amplifier, transistors, filters, etc), as is well-known in the art. It should be emphasized that the invention is not limited to digital signal processing, but could be fully implemented by a combination of analog devices.

While the invention has been described in connection with what is presently considered to be the most practical and preferred embodiments, it is to be understood that the invention is not to be limited to the disclosed embodiments, but on the contrary, is intended to cover various modifications and equivalent arrangements included within the spirit and the scope of the appended claims.

For example, the analysis of the ratio R as described in relation to FIGS. 10A-10C is equally applicable to a ratio of efficiency values obtained by the above-mentioned bolus technique. Furthermore, the foregoing description readily enables the skilled person to design a connection test that is based on other evaluation change parameters than the ratio R, e.g. a difference between efficiency values computed for the first and second operating states, based on either the bolus technique or the non-bolus technique.

Further, it is conceivable that the machine 1 is switched between the first and second operating states by manual intervention, instead of by control signal C3. For example, the control unit 15 may instruct the operator, via the UI device 16 and before step 53, to manually execute a reversal of the blood pump 5.

Even if the foregoing embodiments give the control unit 15 the ability to set the measured property of the treatment fluid, by the control signal C4, the connection test 40 may be implemented also for embodiments that lack this ability, e.g. if the source 6 is configured to supply a ready-made treatment fluid of predefined composition.

The invention claimed is:

1. A control device for a blood treatment machine, wherein the blood treatment machine comprises:
    an extracorporeal blood flow circuit with first and second access devices for connection to upstream and downstream portions, respectively, of a vascular access of a patient and having a blood pump operable to generate a flow of blood in the extracorporeal blood flow circuit from one of the first and second access devices through a blood compartment of a dialyzer and to another of the first and second access devices; and
    a treatment fluid flow circuit configured to generate a flow of treatment fluid through a treatment fluid compartment of the dialyzer, said treatment fluid compartment being separated from the blood compartment by a semi-permeable membrane,
    wherein said control device is configured to, during a connection test:
    cause the blood treatment machine to switch between a first operating state in which the blood pump is operated in a default direction to pump the blood from the first access device through the blood compartment of the dialyzer to the second access device, and a second operating state in which the blood pump is operated in a reverse direction to pump the blood from the second access device through the blood compartment of the dialyzer to the first access device,
    acquire an output signal of at least one sensor in the blood treatment machine,
    compute, based on the output signal, an efficiency change parameter that represents a change in in-vivo clearance of the blood treatment machine during the switch of the blood treatment machine between the first and second operating states, and
    evaluate the efficiency change parameter to determine if the first or second operating state involves a dual fault condition comprising both a co-current dialyzer configuration, in which the flow of blood through the blood compartment and the flow of treatment fluid through the treatment fluid compartment are in a common direction along the semi-permeable membrane, and a reversed access device configuration, in which the first and second access devices are connected to the downstream and upstream portions, respectively, of the vascular access.

2. The control device of claim 1, which is further configured to generate a warning signal indicating that the blood treatment machine has failed the connection test, if the first operating state is determined to involve the dual fault condition.

3. The control device of claim 1, which is operatively associated with an interface device configured to output instructions for an operator of the blood treatment machine, wherein the control device is configured to, if the first operating state is determined to involve the dual fault condition, operate the interface device to instruct the operator to change a connection of the treatment fluid flow circuit or the extracorporeal blood flow circuit to the dialyzer, and change a connection of the first and second access devices to the vascular access.

4. The control device of claim 1, which is further configured to generate a confirmation signal indicating that the blood treatment machine has passed the connection test, if the second operating state is determined to involve the dual fault condition.

5. The control device of claim 1, which is further configured to selectively enable the blood treatment machine to perform a blood treatment session, if the second operating state is determined to involve the dual fault condition.

6. The control device of claim 1, which is further configured to compare the efficiency change parameter to a first range indicating the dual fault condition in the first operating state, a second range indicating the dual fault condition in the second operating state, a third range indicating the co-current dialyzer configuration and not the reversed access device configuration in the first operating state, and a fourth range indicating the reversed access device configuration and not the co-current dialyzer configuration in the first operating state.

7. The control device of claim 6, which is further configured to obtain status values defining one or more of an estimated cardiac output of the patient, an estimated blood flow rate in the vascular access of the patient, a mass transfer area coefficient of the dialyzer, a flow rate of blood through the blood compartment of the dialyzer during the first and second operating states, and a flow rate of treatment fluid through the treatment fluid compartment of the dialyzer during the first and second operating states, and determine at least one of the first, second, third, or fourth ranges as a function of the status values.

8. The control device of claim 1, which is further configured to evaluate the efficiency change parameter to determine if the first and second operating states involve a respective single fault condition comprising either the co-current dialyzer configuration or the reversed access device configuration.

9. The control device of claim 8, which is further configured to generate a warning signal for an operator of the blood treatment machine, if the first and second operating states are determined to involve the single fault condition.

10. The control device of claim 8, which is configured to, if the first and second operating states are determined to involve the single fault condition, instruct the operator to check connections of the treatment fluid flow circuit and the extracorporeal blood flow circuit to the dialyzer and a connection of the first and second access devices to the vascular access.

11. The control device of claim 8, which is further configured to compare the efficiency change parameter to a first range indicating the dual fault condition in the first operating state, a second range indicating the dual fault condition in the second operating state, and a third range indicating the single fault condition in each of the first and second operating states.

12. The control device of claim 11, wherein a fourth range is defined between the first and third ranges, and a fifth range is defined between the second and third ranges, and wherein the control device is further configured to, if the efficiency change parameter falls within the fourth or fifth ranges, instruct the operator to indicate a mass transfer area coefficient of the dialyzer.

13. The control device of claim 1, which is further configured to obtain dedicated connection test settings for the blood pump and the treatment fluid flow circuit and apply the dedicated connection test settings for controlling the blood pump and the treatment fluid flow circuit during the first and second operation states.

14. The control device of claim 13, which is configured to apply the dedicated connection test settings to cause the blood pump, by a control signal, to generate a fixed and predefined flow rate of blood through the dialyzer during the first and second operating states, and to cause the treatment fluid flow circuit, by a further control signal, to generate a fixed and predefined flow rate of treatment fluid through the dialyzer during the first and second operating states.

15. The control device of claim 14, wherein the predefined flow rate of blood is in the approximate range of 200 to 300 ml/min.

16. The control device of claim 14, wherein the predefined flow rate of treatment fluid is in the approximate range of 200 to 400 ml/min.

17. The control device of claim 14, which is further configured to cause the treatment fluid flow circuit, by the further control signal, to generate a fixed fluid property of the treatment fluid, as measured by the at least one sensor, during the first and second operating states.

18. The control device of claim 1, which is configured to compute the efficiency change parameter to represent a ratio of the in-vivo clearance of the blood treatment machine in the first and second operating states.

19. The control device of claim 1, wherein the output signal represents a physical and/or chemical property of the treatment fluid measured by the at least one sensor downstream or upstream of the dialyzer in the treatment fluid flow circuit.

20. The control device of claim 1, wherein the output signal represents at least one of a temperature or a concentration of a substance that is present in the blood and is capable of exchanging across the semi-permeable membrane.

21. The control device of claim 1, wherein said at least one sensor includes a sensor from the group consisting of: a concentration sensor, a temperature sensor, a conductivity sensor, an optical absorbance sensor, a polarimetry sensor, and a density sensor.

22. A blood treatment machine comprising the control device according to claim 1.

23. A method of performing a connection test of a blood treatment machine comprising an extracorporeal blood flow circuit with first and second access devices for connection to upstream and downstream portions of a vascular access of a patient and having a blood pump operable to generate a flow of blood in the extracorporeal blood flow circuit from one of the first and second access devices through a blood compartment of a dialyzer and to another of the first and second access devices, and a treatment fluid flow circuit configured to generate a flow of treatment fluid through a treatment fluid compartment of the dialyzer, said treatment fluid compartment being separated from the blood compartment by a semi-permeable membrane, said method comprising:
    switching the blood treatment machine between a first operating state in which the blood pump is operated in a default direction to pump the blood from the first access device through the blood compartment of the dialyzer to the second access device, and a second operating state in which the blood pump is operated in a reverse direction to pump the blood from the second access device through the blood compartment of the dialyzer to the first access device;
    computing, based on an output signal of at least one sensor in the blood treatment machine, an efficiency change parameter that represents a change in in-vivo clearance of the blood treatment machine when switched between the first and second operating states; and
    evaluating the efficiency change parameter to determine if the first or second operating state involves a dual fault condition comprising both a co-current dialyzer configuration, in which the flow of blood through the blood compartment and the flow of treatment fluid through the treatment fluid compartment are in a common direction along the semi-permeable membrane, and a reversed access device configuration, in which the first and second access devices are connected to the downstream and upstream portions, respectively, of the vascular access.

24. A computer-readable medium comprising computer instructions which, when executed by a processor, cause the processor to perform the method of claim 23.

* * * * *